(12) United States Patent
Kelliher et al.

(10) Patent No.: US 9,321,715 B2
(45) Date of Patent: Apr. 26, 2016

(54) SIMULATED MOVING BED CHROMATOGRAPHIC SEPARATION PROCESS

(75) Inventors: Adam Kelliher, London (GB); Angus Morrison, Isle of Lewis (GB); Anil Oroskar, Lombard, IL (US); Rakesh Vikraman Nair Rema, Lombard, IL (US); Abhilesh Agarwal, Lombard, IL (US)

(73) Assignee: BASF Pharma (Callanish) Limited, Cheshire (GB)

( * ) Notice: Subject to any disclaimer, the term of this patent is extended or adjusted under 35 U.S.C. 154(b) by 546 days.

(21) Appl. No.: 13/519,618

(22) PCT Filed: Dec. 24, 2010

(86) PCT No.: PCT/GB2010/002339
§ 371 (c)(1),
(2), (4) Date: Sep. 13, 2012

(87) PCT Pub. No.: WO2011/080503
PCT Pub. Date: Jul. 7, 2011

(65) Prior Publication Data
US 2012/0330043 A1 Dec. 27, 2012

Related U.S. Application Data

(60) Provisional application No. 61/291,184, filed on Dec. 30, 2009.

(30) Foreign Application Priority Data

Dec. 30, 2009 (GB) .................................. 0922707.5
Sep. 14, 2010 (GB) .................................. 1015343.5

(51) Int. Cl.
*C11B 7/00* (2006.01)
*A23D 9/00* (2006.01)
(Continued)

(52) U.S. Cl.
CPC ............. *C07C 51/47* (2013.01); *C07C 57/03* (2013.01); *C11B 3/10* (2013.01); *C11B 3/12* (2013.01); *B01D 15/185* (2013.01)

(58) Field of Classification Search
CPC ........ C11B 3/10; C11B 7/0008; C07C 51/47; C07C 67/56; C07C 57/03; C07C 69/587; C11C 1/08; A23D 9/00; A01H 5/10; A23L 1/3008

USPC .................................................. 554/193, 224
See application file for complete search history.

(56) References Cited

U.S. PATENT DOCUMENTS

| 2,985,589 A | 5/1931 | Broughton et al. |
| 3,696,107 A | 10/1972 | Neuzil |

(Continued)

FOREIGN PATENT DOCUMENTS

| EP | 1106602 A1 | 6/2001 |
| EP | 1157692 A1 | 11/2001 |

(Continued)

OTHER PUBLICATIONS

Xie Yet al: "Standing Wave Design and Experimental Validation of a Tandem Simulated Moving Bed Process for Insulin Purification", Biotechnology Progress, vol. 18, No. 6, Jan. 1, 2002, pp. 1332-1344.*

(Continued)

*Primary Examiner* — Deborah D Carr
(74) *Attorney, Agent, or Firm* — Servilla Whitney LLC

(57) ABSTRACT

The present invention provides a chromatographic separation process for recovering a polyunsaturated fatty acid (PUFA) product, from a feed mixture, which process comprises introducing the feed mixture to a simulated or actual moving bed chromatography apparatus having a plurality of linked chromatography columns containing, as eluent, an aqueous alcohol, wherein the apparatus has a plurality of zones comprising at least a first zone and second zone, each zone having an extract stream and a raffinate stream from which liquid can be collected from said plurality of linked chromatography columns, and wherein (a) a raffinate stream containing the PUFA product together with more polar components is collected from a column in the first zone and introduced to a nonadjacent column in the second zone, and/or (b) an extract stream containing the PUFA product together with less polar components is collected from a column in the second zone and introduced to a nonadjacent column in the first zone, said PUFA product being separated from different components of the feed mixture in each zone.

27 Claims, 15 Drawing Sheets

(51) Int. Cl.
*C07C 51/47* (2006.01)
*C11B 3/12* (2006.01)
*C07C 57/03* (2006.01)
*C11B 3/10* (2006.01)
*B01D 15/18* (2006.01)

(56) References Cited

U.S. PATENT DOCUMENTS

| | | |
|---|---|---|
| 3,706,812 A | 12/1972 | Rosset et al. |
| 3,761,533 A | 9/1973 | Morit et al. |
| 4,036,745 A | 7/1977 | Broughton |
| 4,048,111 A | 9/1977 | Rosback et al. |
| 4,048,205 A | 9/1977 | Neuzil et al. |
| 4,049,688 A | 9/1977 | Neuzil et al. |
| 4,313,015 A | 1/1982 | Broughton |
| 4,329,280 A | 5/1982 | Cleary et al. |
| 4,353,838 A | 10/1982 | Cleary et al. |
| 4,353,839 A | 10/1982 | Cleary et al. |
| 4,404,145 A | 9/1983 | Cleary et al. |
| 4,433,195 A | 2/1984 | Kulprathipanja |
| 4,486,618 A | 12/1984 | Kulprathipanja et al. |
| 4,495,106 A | 1/1985 | Cleary et al. |
| 4,511,514 A | 4/1985 | Cleary et al. |
| 4,519,952 A | 5/1985 | Cleary et al. |
| 4,521,343 A | 6/1985 | Chao et al. |
| 4,522,761 A | 6/1985 | Cleary et al. |
| 4,524,029 A | 6/1985 | Cleary et al. |
| 4,524,030 A | 6/1985 | Cleary et al. |
| 4,524,049 A | 6/1985 | Cleary et al. |
| 4,529,551 A | 7/1985 | Cleary et al. |
| 4,560,675 A | 12/1985 | Cleary et al. |
| 4,605,783 A | 8/1986 | Zinnen |
| 4,720,579 A | 1/1988 | Kulprathipanja |
| 4,764,276 A | 8/1988 | Berry et al. |
| 4,882,065 A | 11/1989 | Barder |
| 4,902,829 A | 2/1990 | Kulprathipanja |
| 4,961,881 A | 10/1990 | Ou |
| 5,068,418 A | 11/1991 | Kulprathipanja et al. |
| 5,068,419 A | 11/1991 | Kulprathipanja et al. |
| 5,069,883 A | 12/1991 | Montonte |
| 5,093,004 A | 3/1992 | Hotier et al. |
| 5,114,590 A | 5/1992 | Hotier et al. |
| 5,179,219 A | 1/1993 | Priegnitz |
| 5,225,580 A | 7/1993 | Zinnen |
| 5,405,534 A | 4/1995 | Ishida et al. |
| 5,422,007 A | 6/1995 | Nicoud et al. |
| 5,502,077 A | 3/1996 | Breivik et al. |
| 5,547,580 A | 8/1996 | Tsujii et al. |
| 5,656,667 A | 8/1997 | Breivik et al. |
| 5,698,594 A | 12/1997 | Breivik et al. |
| 5,719,302 A * | 2/1998 | Perrut et al. .......... 554/191 |
| 5,777,141 A | 7/1998 | Brunner et al. |
| 5,840,181 A | 11/1998 | Patton et al. |
| 5,917,068 A | 6/1999 | Barnicki |
| 5,945,318 A | 8/1999 | Breivik et al. |
| 6,013,186 A | 1/2000 | Patton et al. |
| 6,063,284 A | 5/2000 | Grill |
| 6,096,218 A | 8/2000 | Hauck et al. |
| 6,204,401 B1 | 3/2001 | Perrut et al. |
| 6,313,330 B1 | 11/2001 | Kiyohara et al. |
| 6,325,898 B1 | 12/2001 | Blehaut et al. |
| 6,350,890 B1 | 2/2002 | Kiy et al. |
| 6,409,923 B1 | 6/2002 | Nicoud et al. |
| 6,413,419 B1 | 7/2002 | Adam et al. |
| 6,471,870 B1 | 10/2002 | Nicoud et al. |
| 6,518,049 B1 | 2/2003 | Haraldsson |
| 6,544,413 B1 | 4/2003 | Nagamatsu et al. |
| 6,713,447 B2 | 3/2004 | Beaudoin et al. |
| 6,789,502 B2 | 9/2004 | Hjaltason et al. |
| 6,863,824 B2 | 3/2005 | Hamende et al. |
| 6,979,402 B1 | 12/2005 | Sprague et al. |
| 7,063,855 B2 | 6/2006 | Hjaltason et al. |
| 7,462,643 B1 | 12/2008 | Pamparana |
| 7,491,522 B2 | 2/2009 | Haraldsson et al. |
| 7,541,480 B2 | 6/2009 | Bruzzese |
| 7,588,791 B2 | 9/2009 | Fabritius et al. |
| 7,667,061 B2 | 2/2010 | Binder et al. |
| 7,678,930 B2 | 3/2010 | Sondbo et al. |
| 7,705,170 B2 | 4/2010 | Geier et al. |
| 7,709,236 B2 | 5/2010 | Akimoto et al. |
| 7,718,698 B2 | 5/2010 | Breivik et al. |
| 7,732,488 B2 | 6/2010 | Breivik et al. |
| 7,807,848 B2 | 10/2010 | Wang |
| 8,063,235 B2 | 11/2011 | Krumbholz et al. |
| 8,216,475 B2 | 7/2012 | Valery et al. |
| 8,282,831 B2 | 10/2012 | Kessler et al. |
| 2002/0011445 A1 | 1/2002 | Lehoucq et al. |
| 2002/0068833 A1 | 6/2002 | Chanteloup et al. |
| 2002/0174769 A1 | 11/2002 | Adam et al. |
| 2003/0006191 A1 | 1/2003 | Heikkila et al. |
| 2003/0216543 A1 | 11/2003 | Wang et al. |
| 2004/0099604 A1 | 5/2004 | Hauck et al. |
| 2005/0087494 A1 | 4/2005 | Hauck et al. |
| 2006/0086667 A1 | 4/2006 | Hauck et al. |
| 2006/0124549 A1 | 6/2006 | Bailly et al. |
| 2007/0068873 A1 | 3/2007 | Oroskar et al. |
| 2007/0148315 A1 | 6/2007 | Schaap et al. |
| 2007/0158270 A1 | 7/2007 | Geier et al. |
| 2007/0181504 A1 | 8/2007 | Binder et al. |
| 2008/0234375 A1 | 9/2008 | Breivik et al. |
| 2009/0023808 A1 | 1/2009 | Raman et al. |
| 2009/0176284 A1 | 7/2009 | Furihata et al. |
| 2010/0012584 A1 | 1/2010 | Majewski et al. |
| 2010/0069492 A1 | 3/2010 | Geiringen et al. |
| 2010/0104657 A1 | 4/2010 | Sondbo et al. |
| 2010/0160435 A1 | 6/2010 | Bruzzese |
| 2010/0163490 A1 | 7/2010 | Lasalle |
| 2010/0190220 A1 | 7/2010 | Furihata et al. |
| 2010/0197785 A1 | 8/2010 | Breivik et al. |
| 2010/0233281 A1 | 9/2010 | Breivik et al. |
| 2010/0267829 A1 | 10/2010 | Breivik et al. |
| 2010/0331559 A1 | 12/2010 | Feist et al. |
| 2010/0331561 A1 | 12/2010 | Schaap et al. |
| 2011/0030457 A1 | 2/2011 | Valery et al. |
| 2011/0091947 A1 | 4/2011 | Kim et al. |
| 2011/0139001 A1 | 6/2011 | Hiliareau et al. |
| 2011/0168632 A1 | 7/2011 | Valery et al. |
| 2012/0214966 A1 | 8/2012 | Theoleyre et al. |
| 2012/0232141 A1 | 9/2012 | Hustvedt et al. |

FOREIGN PATENT DOCUMENTS

| | | |
|---|---|---|
| EP | 1128881 B1 | 6/2005 |
| FR | 2897238 A1 | 8/2007 |
| JP | 58088339 A1 | 5/1983 |
| JP | 58109444 A1 | 6/1983 |
| JP | S61-192797 | 8/1986 |
| JP | S6388159 | 4/1988 |
| JP | H01-197596 | 8/1989 |
| JP | H04-235701 | 8/1992 |
| JP | 06287594 A1 | 10/1994 |
| JP | 09157684 A1 | 6/1997 |
| JP | H10-310555 | 11/1998 |
| JP | 2001139981 A1 | 5/2001 |
| WO | 8703899 A1 | 7/1987 |
| WO | WO-98/32514 | 7/1998 |
| WO | 0187451 A2 | 11/2001 |
| WO | WO-01/87452 | 11/2001 |
| WO | 2007093690 A1 | 8/2007 |
| WO | 2008107562 A2 | 9/2008 |
| WO | 2008149177 A2 | 12/2008 |
| WO | 2009047408 A1 | 4/2009 |
| WO | 2010119319 A1 | 10/2010 |
| ZA | 8905758 | 4/1990 |

OTHER PUBLICATIONS

Xie, Y; Mun, S; Kim, J; and Wang, N, "Standing Wave Design and Experimental Validation of a Tandem Simulated Moving Bed Process for Insulin Purification," Biotechnology Progress, American Instituted of Chemical Engineers, US, vol. 18, No. 6, Jan. 1, 2002, pp. 1332-1344.

(56) References Cited

OTHER PUBLICATIONS

Szepesy, L; Sebestyen, Z; Feher, I; and Nagy, Z, "Continuous Liquid Chromatography," Journal of Chromatography, Elsevier Scientific Publishing Co., Amsterdam, vol. 108, 1975, pp. 285-297.

Quan, Wenqin et al., "Determination of eicosapentaenoic acid and docosahexanoic acid in fish oil by high performance liquid chromatography/mass spectrometry", *Food & Machinery*, vol. 24, No. 2, pp. 114-117. Mar. 31, 2008, 4 pages.

Quan, Wenqin, "Study on the enrichment of glyceride of ω-3PUFA", *Chinese Master's Theses Full-text Database Basic Sciences*, A0062-42 Mar. 15, 2009, 77 pages.

Non-Final Office Action in U.S. Appl. No. 13/880,150, dated Oct. 9, 2015, 20 pages.

\* cited by examiner

Zone 1 Extract - "less polar" components

Zone 1 Raffinate - EPA + "more polar" components

Zone 2 Extract - EPA-EE

Zone 2 Raffinate - "more polar" components

Zone 2 Extract – 97% DHA

High purity DHA produced from non-distilled starting material no evidence of isomeric damage High purity DHA product from distilled starting material containg 1.5% isomeric impurities(total of 4 peaks by GC FAMEs)

SIMULATED MOVING BED CHROMATOGRAPHIC SEPARATION PROCESS

The present invention relates to an improved chromatographic fractionation process for purifying polyunsaturated fatty acids (PUFAs) and derivatives thereof. In particular, the present invention relates to an improved simulated or actual moving bed chromatographic separation process for purifying PUFAs and derivatives thereof.

Fatty acids, in particular PUFAs, and their derivatives are precursors for biologically important molecules, which play an important role in the regulation of biological functions such as platelet aggregation, inflammation and immunological responses. Thus, PUFAs and their derivatives may be therapeutically useful in treating a wide range of pathological conditions including CNS conditions; neuropathies, including diabetic neuropathy; cardiovascular diseases; general immune system and inflammatory conditions, including inflammatory skin diseases.

PUFAs are found in natural raw materials, such as vegetable oils and marine oils. Such PUFAs are however, frequently present in such oils in admixture with saturated fatty acids and numerous other impurities. PUFAs should therefore desirably be purified before nutritional or pharmaceutical uses.

Unfortunately, PUFAs are extremely fragile. Thus, when heated in the presence of oxygen, they are prone to isomerization, peroxidation and oligomerization. The fractionation and purification of PUFA products to prepare pure fatty acids is therefore difficult. Distillation, even under vacuum, can lead to non-acceptable product degradation.

Simulated and actual moving bed chromatography are known techniques, familiar to those of skill in the art. The principle of operation involves countercurrent movement of a liquid eluent phase and a solid adsorbent phase. This operation allows minimal usage of solvent making the process economically viable. Such separation technology has found several applications in diverse areas, including hydrocarbons, industrial chemicals, oils, sugars and APIs. Such separation technology has also been applied to purify PUFAs and their derivatives.

As is well known, in a conventional stationary bed chromatographic system, a mixture whose components are to be separated percolates through a container. The container is generally cylindrical, and is typically referred to as the column. The column contains a packing of a porous material (generally called the stationary phase) exhibiting a high permeability to fluids. The percolation velocity of each component of the mixture depends on the physical properties of that component so that the components exit from the column successively and selectively. Thus, some of the components tend to fix strongly to the stationary phase and thus will percolate slowly, whereas others tend to fix weakly and exit from the column more quickly. Many different stationary bed chromatographic systems have been proposed and are used for both analytical and industrial production purposes.

In contrast, a simulated moving bed system consists of a number of individual columns containing adsorbent which are connected together in series. Eluent is passed through the columns in a first direction. The injection points of the feedstock and the eluent, and the separated component collection points in the system, are periodically shifted by means of a series of valves. The overall effect is to simulate the operation of a single column containing a moving bed of the solid adsorbent. Thus, a simulated moving bed system consists of columns which, as in a conventional stationary bed system, contain stationary beds of solid adsorbent through which eluent is passed, but in a simulated moving bed system the operation is such as to simulate a continuous countercurrent moving bed.

Processes and equipment for simulated moving bed chromatography are described in several patents, including U.S. Pat. No. 2,985,589, U.S. Pat. No. 3,696,107, U.S. Pat. No. 3,706,812, U.S. Pat. No. 3,761,533, FR-A-2103302, FR-A-2651148 and FR-A-2651149, the entirety of which are incorporated herein by reference. The topic is also dealt with at length in "Preparative and Production Scale Chromatography", edited by Ganetsos and Barker, Marcel Dekker Inc, New York, 1993, the entirety of which is incorporated herein by reference.

An actual moving bed system is similar in operation to a simulated moving bed system. However, rather than shifting the injection points of the feed mixture and the eluent, and the separated component collection points by means of a system of valves, instead a series of adsorption units (i.e. columns) are physically moved relative to the feed and drawoff points. Again, operation is such as to simulate a continuous countercurrent moving bed.

Processes and equipment for actual moving bed chromatography are described in several patents, including U.S. Pat. No. 6,979,402, U.S. Pat. No. 5,069,883 and U.S. Pat. No. 4,764,276, the entirety of which are incorporated herein by reference.

Simulated and actual moving bed technology is generally only suitable for separating binary mixtures. Thus, a more polar component will move with the eluent, and be collected as a raffinate stream, and a less polar component will move with the adsorbent, and be collected as an extract stream. It is therefore difficult to use simulated or actual moving bed technology to separate a desired product from a crude mixture containing both polar and non-polar impurities. This limits the applicability of such techniques in purifying PUFA products from fish oils, for example.

Accordingly, when simulated or actual moving bed technology has been used to separate PUFAs from natural oils in the past, it is generally necessary first to subject the natural oil to a preliminary separation step (e.g. fixed column chromatography) before purifying the intermediate product obtained using simulated or actual moving bed technology (see, for example, EP-A-0697034). Typically, the initial purification step removes polar or non-polar components, thus creating an essentially binary mixture which is then subjected to moving bed chromatography.

This process of separating a binary mixture is illustrated with reference to FIG. 1. The concept of a simulated or actual continuous countercurrent chromatographic separation process is explained by considering a vertical chromatographic column containing stationary phase S divided into sections, more precisely into four superimposed sub-zones I, II, III and IV going from the bottom to the top of the column. The eluent is introduced at the bottom at IE by means of a pump P. The mixture of the components A and B which are to be separated is introduced at IA+B between sub-zone II and sub-zone III. An extract containing mainly B is collected at SB between sub-zone I and sub-zone II, and a raffinate containing mainly A is collected at SA between sub-zone III and sub-zone IV.

In the case of a simulated moving bed system, a simulated downward movement of the stationary phase S is caused by movement of the introduction and collection points relative to the solid phase. In the case of an actual moving bed system, downward movement of the stationary phase S is caused by movement of the various chromatographic columns relative to the introduction and collection points. In FIG. 1, eluent flows upward and mixture A+B is injected between sub-zone II and sub-zone III. The components will move according to their chromatographic interactions with the stationary phase, for example adsorption on a porous medium. The component B that exhibits stronger affinity to the stationary phase (the slower running component) will be more slowly entrained by the eluent and will follow it with delay. The component A that exhibits the weaker affinity to the stationary phase (the faster running component) will be easily entrained by the eluent. If the right set of parameters, especially the flow rate in each zone, are correctly estimated and controlled, the component A exhibiting the weaker affinity to the stationary phase will be collected between sub-zone III and sub-zone IV as a raffinate and the component B exhibiting the stronger affinity to the stationary phase will be collected between sub-zone I and sub-zone II as an extract.

It will therefore be appreciated that the conventional moving bed system schematically illustrated in FIG. 1 is limited to binary fractionation.

Accordingly, there is a need for a single simulated or actual moving bed chromatographic separation process that can separate PUFAs or their derivatives from both faster and slower running components (i.e. more polar and less polar impurities), to produce an essentially pure PUFA or derivative thereof. It is further desirable that the process should involve inexpensive eluents which operate under standard temperature and pressure conditions.

It has now been surprisingly found that a PUFA product can be effectively purified with a single simulated or actual moving bed apparatus using an aqueous alcohol eluent. The present invention therefore provides a chromatographic separation process for recovering a polyunsaturated fatty acid (PUFA) product, from a feed mixture, which process comprises introducing the feed mixture to a simulated or actual moving bed chromatography apparatus having a plurality of linked chromatography columns containing, as eluent, an aqueous alcohol, wherein the apparatus has a plurality of zones comprising at least a first zone and second zone, each zone having an extract stream and a raffinate stream from which liquid can be collected from said plurality of linked chromatography columns, and wherein (a) a raffinate stream containing the PUFA product together with more polar components is collected from a column in the first zone and introduced to a nonadjacent column in the second zone, and/or (b) an extract stream containing the PUFA product together with less polar components is collected from a column in the second zone and introduced to a nonadjacent column in the first zone, said PUFA product being separated from different components of the feed mixture in each zone.

Also provided is a PUPA product obtainable by the process of the present invention.

The PUFA products produced by the process of the present invention are produced in high yield, and have high purity. Further, the content of the distinctive impurities which typically arise from distillation of PUFAs is very low. As used herein, the term "isomeric impurities" is used to denote those impurities typically produced during the distillation of PUFA-containing natural oils. These include PUFA isomers, peroxidation and oligomerization products.

Figure 1:
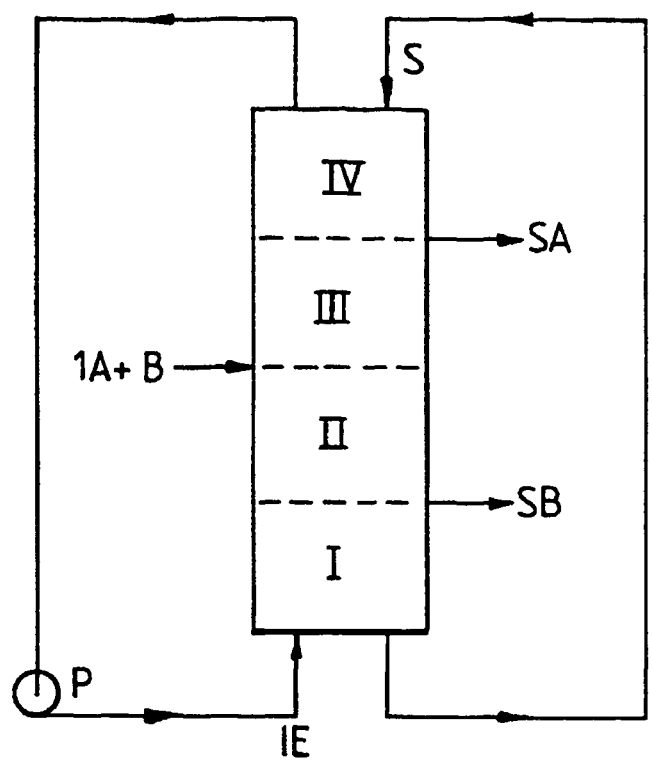
FIG. 1 illustrates the basic principles of a simulated or actual moving bed process for separating a binary mixture.

The term "polyunsaturated fatty acid" (PUFA) refers to fatty acids that contain more than one double bond. Such PUFAs are well known to the person skilled in the art. As used herein, a PUFA derivative is a PUFA in the form of a mono-, di- or triglyceride, ester, phospholipid, amide, lactone, or salt. Triglycerides and esters are preferred. Esters are more preferred. Esters are typically alkyl esters, preferably $C_1$-$C_6$ alkyl esters, more preferably $C_1$-$C_4$ alkyl esters. Examples of esters include methyl and ethyl esters. Ethyl esters are most preferred.

As used herein, the term "PUFA product" refers to a product comprising one or more polyunsaturated fatty acids (PUFAs), and/or derivatives thereof, typically of nutritional or pharmaceutical significance. Typically, the PUFA product is a single PUFA or derivative thereof. Alternatively, the PUFA product is a mixture of two or more PUFAs or derivatives thereof, for example two.

As used herein, the term "zone" refers to a plurality of linked chromatography columns containing, as eluent, an aqueous alcohol, and having one or more injection points for a feed mixture stream, one or more injection points for water and/or alcohol, a raffinate take-off stream from which liquid can be collected from said plurality of linked chromatography columns, and an extract take-off stream from which liquid can be collected from said plurality of linked chromatography columns. Typically, each zone has only one injection point for a feed mixture. In one embodiment, each zone has only one injection point for the aqueous alcohol eluent. In another embodiment, each zone has two or more injection points for water and/or alcohol.

The term "raffinate" is well known to the person skilled in the art. In the context of actual and simulated moving bed chromatography it refers to the stream of components that move more rapidly with the liquid eluent phase compared with the solid adsorbent phase. Thus, a raffinate stream is typically enriched with more polar components, and depleted of less polar components compared with a feed stream.

The term "extract" is well known to the person skilled in the art. In the context of actual and simulated moving bed chromatography it refers to the stream of components that move more rapidly with the solid adsorbent phase compared with the liquid eluent phase. Thus, an extract stream is typically enriched with less polar components, and depleted of more polar components compared with a feed stream.

As used herein the term "nonadjacent" when applied to columns in the same apparatus refers to columns separated by one or more columns, preferably 3 or more columns, more preferably 5 or more columns, most preferably about 5 columns.

Thus, where (a) a raffinate stream containing the PUFA product together with more polar components is collected from a column in the first zone and introduced to a nonadjacent column in the second zone, the raffinate stream collected from the first zone is the feed mixture for the second zone. Where (b) an extract stream containing the PUFA product together with less polar components is collected from a column in the second zone and introduced to a nonadjacent column in the first zone, the extract stream collected from the second zone is the feed mixture in the first zone.

Typically, the PUFA product comprises at least one ω-3 or ω-6 PUFA, preferably at least one ω-3 PUFA. Examples of ω-3 PUFAs include alpha-linolenic acid (ALA), stearidonic acid (SDA), eicosatrienoic acid (ETE), eicosatetraenoic acid (ETA), eicosapentaenoic acid (EPA), docosapentaenoic acid (DPA) and docosahexaenoic acid (DHA). SDA, EPA, DPA and DHA are preferred. EPA and DHA are more preferred. Examples of ω-6 PUFAs include linoleic acid (LA), gamma-linolenic acid (GLA), eicosadienoic acid, dihomo-gamma-linolenic acid (DGLA), arachidonic acid (ARA), docosadienoic acid, adrenic acid and docosapentaenoic (ω-6) acid. LA, ARA, GLA and DGLA are preferred.

In one embodiment, the PUFA product is EPA and/or EPA ethyl ester (EE)

In another embodiment, the PUFA product is DHA and/or EPA ethyl ester (EE).

In a yet further embodiment, the PUFA product is a mixture of EPA and DHA and/or EPA EE and DHA EE.

Suitable feed mixtures for fractionating by the process of the present invention may be obtained from natural sources including vegetable and animal oils and fats, and from synthetic sources including oils obtained from genetically modified plants, animals and micro organisms including yeasts. Examples include fish oils, algal and microalgal oils and plant oils, for example borage oil, Echium oil and evening primrose oil. In one embodiment, the feed mixture is a fish oil. In another embodiment, the feed mixture is an algal oil. Algal oils are particularly suitable when the desired PUFA product is EPA and/or DHA. Genetically modified Safflower oil is particularly suitable when the desired PUFA product is GLA. Genetically modified yeast is particularly suitable when the desired PUFA product is EPA.

The feed mixture may undergo chemical treatment before fractionation by the process of the invention. For example, it may undergo glyceride transesterification or glyceride hydrolysis followed in certain cases by selective processes such as crystallisation, molecular distillation, urea fractionation, extraction with silver nitrate or other metal salt solutions, iodolactonisation or supercritical fluid fractionation.

The feed mixtures typically contain the PUFA product and at least one more polar component and at least one less polar component. The less polar components have a stronger adherence to the adsorbent used in the process of the present invention than does the PUFA product. During operation, such less polar components typically move with the solid adsorbent phase in preference to the liquid eluent phase. The more polar components have a weaker adherence to the adsorbent used in the process of the present invention than does the PUFA product. During operation, such more polar components typically move with the liquid eluent phase in preference to the solid adsorbent phase. In general, more polar components will be separated into a raffinate stream, and less polar components will be separated into an extract stream.

Examples of the more and less polar components include (1) other compounds occurring in natural oils (e.g. marine oils or vegetable oils), (2) byproducts formed during storage, refining and previous concentration steps and (3) contaminants from solvents or reagents which are utilized during previous concentration or purification steps.

Examples of (1) include other unwanted PUFAs; saturated fatty acids; sterols, for example cholesterol; vitamins; and environmental pollutants, such as polychlorobiphenyl (PCB), polyaromatic hydrocarbon (PAH) pesticides, chlorinated pesticides, dioxines and heavy metals. PCB, PAH, dioxines and chlorinated pesticides are all highly non-polar components.

Examples of (2) include isomers and oxidation or decomposition products from the PUFA product, for instance, autooxidation polymeric products of fatty acids or their derivatives.

Examples of (3) include urea which may be added to remove saturated or mono-unsaturated fatty acids from the feed mixture.

Preferably, the feed mixture is a PUFA-containing marine oil, more preferably a marine oil comprising EPA and/or DHA.

A typical feed mixture for preparing concentrated EPA by the process of the present invention comprises 50-75% EPA, 0 to 10% DHA, and other components including other essential ω-3 and ω-6 fatty acids.

A preferred feed mixture for preparing concentrated EPA by the process of the present invention comprises 55% EPA, 5% DHA, and other components including other essential ω-3 and ω-6 fatty acids. DHA is less polar than EPA.

A typical feed mixture for preparing concentrated DHA by the process of the present invention comprises 50-75% DHA, 0 to 10% EPA, and other components including other essential ω-3 and ω-6 fatty acids.

A preferred feed mixture for preparing concentrated DHA by the process of the present invention comprises 75% DHA, 7% EPA and other components including other essential ω-3 and ω-6 fatty acids. EPA is more polar than DHA.

A typical feed mixture for preparing a concentrated mixture of EPA and DHA by the process of the present invention comprises greater than 33% EPA, and greater than 22% DHA.

The process of the invention requires a plurality of zones in said chromatography apparatus. Typically, two or more zones are used. The number of zones is not particularly limited, but in general there are 2 to 5 zones. Preferably, there are two or three zones, more preferably there are two zones.

Typically, the components separated in each zone of the apparatus used in the process of the present invention have different polarities.

Typically, a) the aqueous alcohol eluent present in each zone has a different water:alcohol ratio; and/or
(b) the rate at which liquid collected via the extract and raffinate streams in each zone is recycled back into the same zone is adjusted such that the PUFA product can be separated from different components of the feed mixture in each zone.

When the apparatus used in the process of the present invention has two zones, the present invention typically provides a chromatographic separation process for recovering a polyunsaturated fatty acid (PUFA) product, from a feed mixture, which process comprises introducing the feed mixture to a simulated or actual moving bed chromatography apparatus having a plurality of linked chromatography columns containing, as eluent, an aqueous alcohol, wherein the apparatus has a first zone and a second zone, each zone having an extract stream and a raffinate stream from which liquid can be collected from said plurality of linked chromatography columns, and wherein (a) a raffinate stream containing the PUFA product together with more polar components is collected from a column in the first zone and introduced to a nonadjacent column in the second zone, and/or (b) an extract stream containing the PUFA product together with less polar components is collected from a column in the second zone and introduced to a nonadjacent column in the first zone, said PUFA product being separated from less polar components of the feed mixture in the first zone, and said PUFA product being separated from more polar components of the feed mixture in the second zone.

Typically, when the apparatus used in the process of the present invention contains two zones, the eluent in the first zone contains more alcohol than the eluent in the second zone, and the second zone is downstream of the first zone with respect to the flow of eluent in the system. Thus, the eluent in the system typically moves from the first zone to the second zone. Conversely, the solid adsorbent phase typically moves from the second zone to the first zone. Typically, the two zones do not overlap, i.e. there are no chromatographic columns which are in both zones.

In a further embodiment of the invention, the apparatus has a first zone, a second zone and a third zone. The water:alcohol ratios of the aqueous alcohol eluent present in the first, second and third zones are typically different. As will be evident to one skilled in the art, this has the consequence that impurities having different polarities can be removed in each zone.

Preferably, when the apparatus has three zones, the eluent in the first zone contains more alcohol than the eluent in the second zone and the third zone and the first zone is upstream of the second and third zones with respect to the flow of eluent in the system. Typically, the eluent in the second zone contains more alcohol than the eluent in the third zone and the second zone is upstream of the third zone with respect to the flow of eluent in the system. Typically, in the first zone, said PUFA product is separated from components of the feed mixture which are less polar than the PUFA product. Typically, in the second zone, said PUFA product is separated from components of the feed mixture which are less polar than the PUFA product but more polar than the components separated in the first zone. Typically, in the third zone, said PUFA product is separated from components of the feed mixture which are more polar than the PUFA product.

In a further embodiment, in the first zone, said PUFA product is separated from components of the feed mixture which are less polar than the PUFA product, in the second zone, said PUFA product is separated from components of the feed mixture which are more polar than the PUFA product, and in the third zone, said PUFA product is separated from components of the feed mixture which are more polar than the PUFA product and also more polar than, the components separated in the second zone.

Such a setup having three zones would be suitable for separating EPA and DHA from a mixture containing impurities which are less polar than DHA and EPA and also containing impurities which are more polar than EPA. In the first zone, the components which are less polar than DHA and EPA are removed as an extract stream and a raffinate stream comprising DHA, EPA and components which are more polar than EPA is collected and introduced into the second zone. In the second zone, DHA is removed as an extract stream and a raffinate stream comprising EPA and components which are more polar than EPA is collected and introduced into the third zone. In the third zone, the components which are more polar than EPA are removed as a raffinate stream and purified EPA is collected as an extract stream. In this embodiment, the purified EPA is the purified PUFA product. Such a setup has an advantage that a secondary PUFA may also be recovered. In this case, the secondary PUFA is the DHA collected as the extract stream from the second zone.

Typically, in addition to said PUFA product, an additional secondary PUFA product is collected in the chromatographic separation process of the invention. Preferably, the PUFA product is EPA and the additional secondary PUFA product is DHA.

In a further embodiment of the invention, the apparatus is configured to collect a PUFA product which is a concentrated mixture of EPA and DHA. Thus, a feed mixture is used which contains EPA, DHA, components which are more polar than EPA and DHA, and components which are less polar than EPA and DHA. In the first zone, less polar material than EPA and DHA is removed. In the second zone, material which is more polar than EPA and DHA is removed, and a concentrated mixture of EPA and DHA is collected as the PUFA product.

Any known simulated or actual moving bed chromatography apparatus may be utilised for the purposes of the method of the present invention, as long as the apparatus is configured with the multiple, in particular two, zones which characterise the process of the present invention. Those apparatuses described in U.S. Pat. No. 2,985,589, U.S. Pat. No. 3,696,107, U.S. Pat. No. 3,706,812, U.S. Pat. No. 3,761,533, FR-A-2103302, FR-A-2651148, FR-A-2651149, U.S. Pat. No. 6,979,402, U.S. Pat. No. 5,069,883 and U.S. Pat. No. 4,764,276 may all be used if configured in accordance with the process of the present invention.

The number of columns used in the apparatus is not particularly limited. A skilled person would easily be able to determine an appropriate number of columns to use. The number of columns is typically 8 or more, preferably 15 or more. In a more preferred embodiment 15 or 16 columns are used. In another more preferred embodiment, 19 or 20 columns are used. In other more preferred embodiments, 30 or more columns are used. Typically, there are no more than 50 columns, preferably no more than 40.

Each zone typically consists of an approximately equal share of the total number of columns. Thus, in the case of an apparatus configured with two zones, each zone typically consists of approximately half of the total number of chromatographic columns in the system. Thus, the first zone typically comprises 4 or more, preferably 8 or more, more preferably about 8 columns. The second zone typically comprises 4 or more, preferably 7 or more, more preferably 7 or 8 columns.

The dimensions of the columns used in the apparatus are not particularly limited, and will depend on the volume of feed mixture to be purified. A skilled person would easily be able to determine appropriately sized columns to use. The diameter of each column is typically between 10 and 500 mm, preferable between 25 and 250 mm, more preferable between 50 and 100 mm, and most preferably between 70 and 80 mm. The length of each column is typically between 10 and 200 cm, preferably between 25 and 150 cm, more preferably between 70 and 110 cm, and most preferably between 80 and 100 cm.

The columns in each zone typically have identical dimensions but may, for certain applications, have different dimensions.

The flow rates to the column are limited by maximum pressures across the series of columns and will depend on the column dimensions and particle size of the solid phases. One skilled in the art will easily be able to establish the required flow rate for each column dimension to ensure efficient desorption. Larger diameter columns will in general need higher flows to maintain linear flow through the columns.

For the typical column sizes outlined above, and for an apparatus having two zones, typically the flow rate of eluent into the first zone is from 1 to 4.5 L/min, preferably from 1.5 to 2.5 L/min. Typically, the flow rate of the extract from the first zone is from 0.1 to 2.5 L/min, preferably from 0.5 to 2.25 L/min. In embodiments where part of the extract from the first zone is recycled back into the first zone, the flow rate of recycle is typically from 0.7 to 1.4 L/min, preferably about 1 L/min. Typically, the flow rate of the raffinate from the first zone is from 0.2 to 2.5 L/min, preferably from 0.3 to 2.0 L/min. In embodiments where part of the raffinate from the first zone is recycled back into the first zone, the flow rate of recycle is typically from 0.3 to 1.0 L/min, preferably about 0.5 L/min. Typically, the flow rate of introduction of the feed mixture into the first zone is from 5 to 150 mL/min, preferably from 10 to 100 mL/min, more preferably from 20 to 60 mL/min.

For the typical column sizes outlined above, and for an apparatus having two zones, typically the flow rate of eluent into the second zone is from 1 to 4 L/min, preferably from 1.5 to 3.5 L/min. Typically, the flow rate of the extract from the second zone is from 0.5 to 2 L/min, preferably from 0.7 to 1.9 L/min. In embodiments where part of the extract from the second zone is recycled back into the second zone, the flow rate of recycle is typically from 0.6 to 1.4 L/min, preferably from 0.7 to 1.1 L/min, more preferably about 0.9 L/min. Typically, the flow rate of the raffinate from the second zone is from 0.5 to 2.5 L/min, preferably from 0.7 to 1.8 L/min, more preferably about 1.4 L/min.

As the skilled person will appreciate, references to rates at which liquid is collected or removed via the various extract and raffinate streams refer to volumes of liquid removed in an amount of time, typically L/minute. Similarly, references to rates at which liquid is recycled back into the same zone, typically to an adjacent column in the same zone, refer to volumes of liquid recycled in an amount of time, typically L/minute.

Typically, part of one or more of the extract stream from the first zone, the raffinate stream from the first zone, the extract stream from the second zone, and the raffinate stream from the second zone are recycled back into the same zone, typically into an adjacent column in the same zone.

This recycle is different from the feeding of an extract or raffinate stream into a non-adjacent column in another zone. Rather, the recycle involves feeding part of the extract or raffinate stream out of a zone back into the same zone, typically into an adjacent column in the same zone.

The rate at which liquid collected via the extract or raffinate stream from the first or second zones is recycled back into the same zone is the rate at which liquid collected via that stream is fed back into the same zone, typically into an adjacent column in the same zone. This can be seen with reference to FIG. 9. The rate of recycle of extract in the first zone is the rate at which extract collected from the bottom of column 2 is fed into the top of column 3, i.e. the flow rate of liquid into the top of column 3. The rate of recycle of extract in the second zone is the rate at which extract collected at the bottom of column 10 is fed into the top of column 11, i.e. the flow rate of liquid into the top of column 11.

Recycle of the extract and/or raffinate streams is typically effected by feeding the liquid collected via that stream into a container, and then pumping an amount of that liquid from the container back into the same zone. In this case, the rate of recycle of liquid collected via a particular extract or raffinate stream, typically back into an adjacent column in the same zone, is the rate at which liquid is pumped out of the container back into the same zone, typically into an adjacent column.

As the skilled person will appreciate, the amount of liquid being introduced into a zone via the eluent and feedstock streams is balanced with the amount of liquid removed from a zone, and recycled back into the same zone. Thus, with reference to FIG. 9, for the extract stream, the flow rate of eluent (desorbent) into the first or second zone (D) is equal to the rate at which liquid collected via the extract stream from that zone accumulates in a container (E1/E2) added to the rate at which extract is recycled back into the same zone (D−E1/D−E2). For the raffinate stream in a zone, the rate at which extract is recycled back into a zone (D−E1/D−E2) added to the rate at which feedstock is introduced into a zone (F/R1) is equal to the rate at which liquid collected via the raffinate stream from that zone accumulates in a container (R1/R2) added to the rate at which raffinate is recycled back into the same zone (D+F−E1−R1/D+R1−E2−R2).

The rate at which liquid collected from a particular extract or raffinate stream from a zone accumulates in a container can also be thought of as the net rate of removal of that extract or raffinate stream from that zone.

Typically, the rate at which liquid collected via the extract stream out of the first zone is recycled back into the first zone differs from the rate at which liquid collected via the extract stream out of the second zone is recycled back into the second zone, and/or the rate at which liquid collected via the raffinate stream out of the first zone is recycled back into the first zone differs from the rate at which liquid collected via the raffinate stream out of the second zone is recycled back into the second zone.

Varying the rate at which liquid collected via the extract and/or raffinate streams in each zone is recycled back into the same zone has the effect of varying the amount of more polar and less polar components present in the other extract and raffinate streams. Thus, for example, a lower extract recycle rate results in fewer of the less polar components in that zone being carried through to the raffinate stream in that zone. A higher extract recycle rate results in more of the less polar components in that zone being carried through to the raffinate stream in that zone. This can be seen, for example, in the specific embodiment of the invention shown in FIG. 6. The rate at which liquid collected via the extract stream in the first zone is recycled back into the same zone (D−E1) will affect to what extent any of component A is carried through to the raffinate stream in the first zone (R1).

Typically, the rate at which liquid collected via the extract stream from the first zone is recycled back into the first zone is faster than the rate at which liquid collected via the extract stream from the second zone is recycled back into the second zone. Preferably, a raffinate stream containing the PUFA product together with more polar components is collected from a column in the first zone and introduced to a nonadjacent column in the second zone, and the rate at which liquid collected via the extract stream from the first zone is recycled back into the first zone is faster than the rate at which liquid collected via the extract stream from the second zone is recycled back into the second zone.

Alternatively, the rate at which liquid collected via the extract stream from the first zone is recycled back into the first zone is slower than the rate at which liquid collected via the extract stream from the second zone is recycled back into the second zone.

Typically, the rate at which liquid collected via the raffinate stream from the second zone is recycled back into the second zone is faster than the rate at which liquid collected via the raffinate stream from the first zone is recycled back into the first zone. Preferably, an extract stream containing the PUFA product together with less polar components is collected from a column in the second zone and introduced to a nonadjacent column in the first zone, and the rate at which liquid collected via the raffinate stream from the second zone is recycled back into the second zone is faster than the rate at which liquid collected via the raffinate stream from the first zone is recycled back into the first zone.

Alternatively, the rate at which liquid collected via the raffinate stream from the second zone is recycled back into the second zone is slower than the rate at which liquid collected via the raffinate stream from the first zone is recycled back into the first zone.

The step time, i.e. the time between shifting the points of injection of the feed mixture and eluent, and the various take off points of the collected fractions, is not particularly limited, and will depend on the number and dimensions of the columns used, and the flow rate through the apparatus. A skilled person would easily be able to determine appropriate step times to use in the process of the present invention. The step time is typically from 100 to 1000 seconds, preferably from 200 to 800 seconds, more preferably from about 250 to about 750 seconds. In some embodiments, a step time of from 100 to 400 seconds, preferably 200 to 300 seconds, more preferably about 250 seconds, is appropriate. In other embodiments, a step time of from 600 to 900 seconds, preferably 700 to 800 seconds, more preferably about 750 seconds is appropriate.

In the process of the present invention, actual moving bed chromatography is preferred.

Conventional adsorbents known in the art for actual and simulated moving bed systems may be used in the process of the present invention. Each chromatographic column may contain the same or a different adsorbent. Typically, each column contains the same adsorbent. Examples of such commonly used materials are polymeric beads, preferably polystyrene reticulated with DVB (divinylbenzene); and silica gel, preferably reverse phase bonded silica gel with C8 or C18 alkanes, especially C18. C18 bonded reverse phase silica gel is preferred. The adsorbent used in the process of the present invention is preferably non-polar.

The shape of the adsorbent stationary phase material may be, for example, spherical or nonspherical beads, preferably substantially spherical beads. Such beads typically have a diameter of 40 to 500 microns, preferably 100 to 500 microns, more preferably 250 to 500 microns, even more preferably 250 to 400 microns, most preferably 250 to 350 microns. These preferred particle sizes are somewhat larger than particle sizes of beads used in the past in simulated and actual moving bed processes. Use of larger particles enables a lower pressure of eluent to be used in the system. This, in turn, has advantages in terms of cost savings, efficiency and lifetime of the apparatus. It has surprisingly been found that adsorbent beads of large particle size may be used in the process of the present invention (with their associated advantages) without any loss in resolution.

The adsorbent typically has a pore size of from 10 to 50 nm, preferably 15 to 45 nm, more preferably 20 to 40 nm, most preferably 25 to 35 nm.

The eluent used in the process of the present invention is an aqueous alcohol. The aqueous alcohol typically comprises water and one or more short chain alcohols. The short chain alcohol typically has from 1 to 6 carbon atoms. Examples of suitable alcohols include methanol, ethanol, n-propanol, i-propanol, n-butanol, i-butanol, s-butanol and t-butanol. Methanol and ethanol are preferred. Methanol is more preferred.

Typically, the eluent is not in a supercritical state. Typically, the eluent is a liquid.

Typically, the average water:alcohol ratio of the eluent in the entire apparatus is from 0.1:99.9 to 9:91 parts by volume, preferably from 0.25:99.75 to 7:93 parts by volume, more preferably from 0.5:99.5 to 6:94 parts by volume.

The eluting power of the eluent in each of the zones is typically different. Preferably, the eluting power of the eluent in the first zone is greater than that of the eluent in the second and subsequent zones. In practice this is achieved by varying the relative amounts of water and alcohol in each zone. Alcohols are generally more powerful desorbers than water. Thus, the amount of alcohol in the eluent in the first zone is typically greater than the amount of alcohol in the eluent of the second and subsequent zones.

In embodiments where the aqueous alcohol present in each zone has a different water alcohol content, the water:alcohol ratio of the eluent in the first zone is typically from 0:100 to 5:95 parts by volume, preferably from 0.1:99.9 to 2.5:97.5 parts by volume, more preferably from 0.25:99.75 to 2:98 parts by volume, and most preferably from 0.5:99.5 to 1.5:98.5 parts by volume. In these embodiments, the water:alcohol ratio of the eluent in the second zone is typically from 3:97 to 7:93 parts by volume, preferably from 4:96 to 6:94 parts by volume, more preferably from 4.5:95.5 to 5.5:94.5 parts by volume.

In a particularly preferred embodiment where the aqueous alcohol present in each zone has a different water alcohol content, the water:alcohol ratio of the eluent in the first zone is from 0.5:99.5 to 1.5:98.5 parts by volume, and the water:alcohol ratio of the eluent in the second zone is from 4.5:95:5 to 5.5:94.5 parts by volume.

In embodiments where the rate at which liquid collected via the extract and raffinate streams in each zone is recycled back into the same zone is adjusted such that the PUFA product can be separated from different components of the feed mixture in each zone, the water:alcohol ratio of the eluents in each zone may be the same or different. Typically, the water:alcohol ratio of the eluent in each zone is from 0.5:99.5 to 5.5:94.5 parts by volume. In one embodiment, the water:alcohol ratio of the eluent in the first zone is lower than the water:alcohol ratio of the eluent in the second zone. In another embodiment, the water:alcohol ratio of the eluent in the first zone is higher than the water:alcohol ratio of the eluent in the second zone. In a further embodiment, the water:alcohol ratio of the eluent in the first zone is the same as the water:alcohol ratio of the eluent in the second zone.

It will be appreciated that the ratios of water and alcohol in each zone referred to above are average ratios within the totality of the zone.

Typically, the water:alcohol ratio of the eluent in each zone is controlled by introducing water and/or alcohol into one or more columns in the zones. Thus, for example, to achieve a lower water:alcohol ratio in the first zone than in the second zone, water is typically introduced more slowly into the first zone than the second zone. In some embodiments, essentially pure alcohol and essentially pure water may be introduced at different points in each zone. The relative flow rates of these two streams will determine the overall solvent profile across the zone. In other embodiments, different alcohol/water mixtures may be introduced at different points in each zone. That will involve introducing two or more different alcohol/water mixtures into the zone, each alcohol/water mixture having a different alcohol:water ratio. The relative flow rates and relative concentrations of the alcohol/water mixtures in this embodiment will determine the overall solvent profile across the zone. In other embodiments where the water:alcohol ratio of the eluent in each zone is the same, the same alcohol/water mixture is introduced to each zone.

Typically, the process of the present invention is conducted at from 15 to 55° C., preferably at from 20 to 40° C., more preferably at about 30° C. Thus, the process is typically carried out at room temperature, but may be conducted at elevated temperatures.

The process of the present invention involves introducing a feed stream into one zone (for example the first zone), collecting a first intermediate stream enriched with the PUFA product and introducing the first intermediate stream into another zone (for example the second zone). Thus, when the apparatus has two zones, the process involves either (a) collecting a first intermediate stream from the first zone and introducing it into the second zone, or (b) collecting a first intermediate stream from the second zone and introducing it into the first zone. In this way, the PUFA product can be separated from both more and less polar components in a single process.

Either (a) a raffinate stream containing the PUFA product together with more polar components is collected from a column in the first zone and introduced to a nonadjacent column in the second zone, or (b) an extract stream containing the PUFA product together with less polar components is collected from a column in the second zone and introduced to a nonadjacent column in the first zone.

In a particularly preferred embodiment, the apparatus has two zones, and the process of the present invention comprises:
  (i) introducing the feed mixture into the first zone, and removing a first raffinate stream enriched with the PUFA product and a first extract stream depleted of the PUFA product, and
  (ii) introducing the first raffinate stream into the second zone, removing a second raffinate stream depleted of the PUFA product, and collecting a second extract stream to obtain the PUFA product.

This particularly preferred embodiment is suitable for purifying EPA from a feed mixture.

Figure 2:
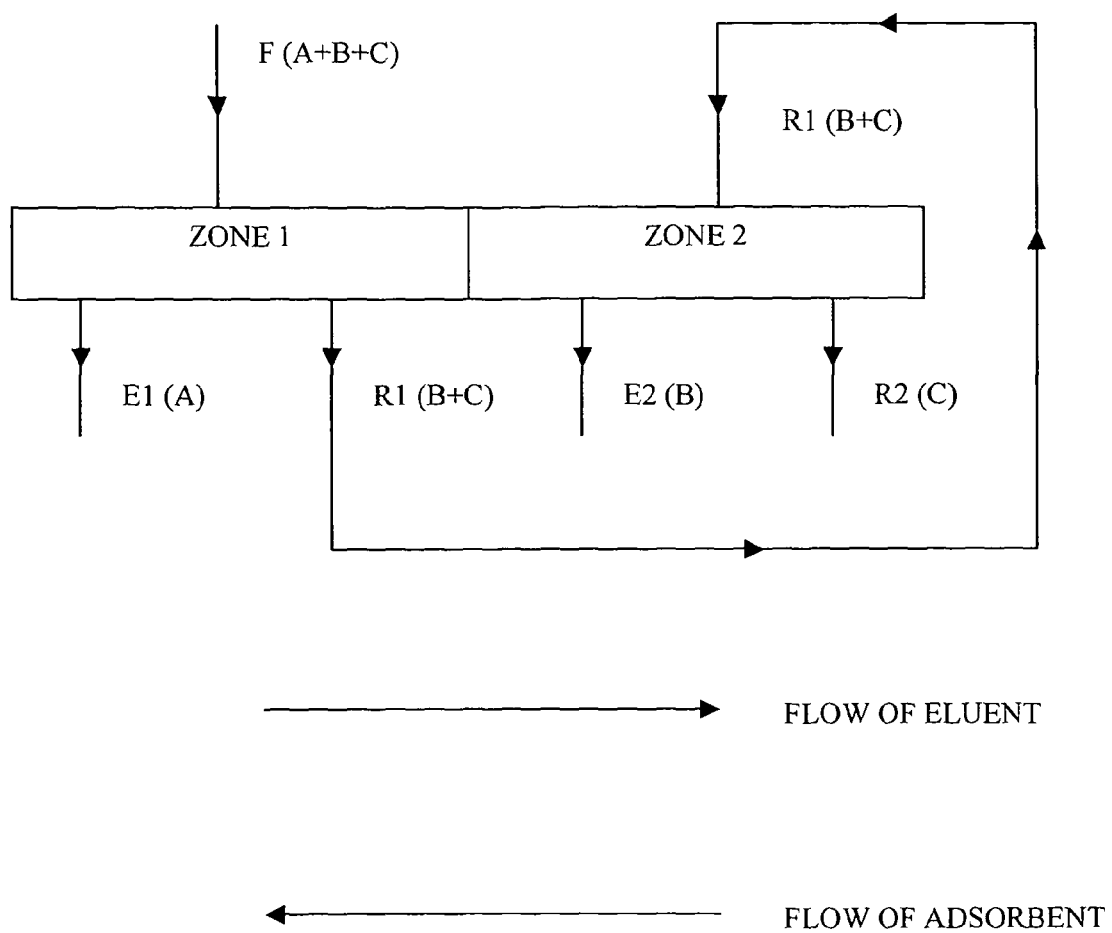
FIG. 2 illustrates a first preferred embodiment of the invention which is suitable for separating EPA from faster and slower running components (i.e. more polar and less polar impurities).

This particularly preferred embodiment is illustrated in FIG. 2. A feed mixture F comprising the PUFA product (B) and more polar (C) and less polar (A) components is introduced into the first zone. In the first zone, the less polar components (A) are removed as extract stream E1. The PUFA product (B) and more polar components (C) are removed as raffinate stream R1. Raffinate stream R1 is then introduced into the second zone. In the second zone, the more polar components (C) are removed as raffinate stream R2. The PUFA product (B) is collected as extract stream E2.

Figure 4:
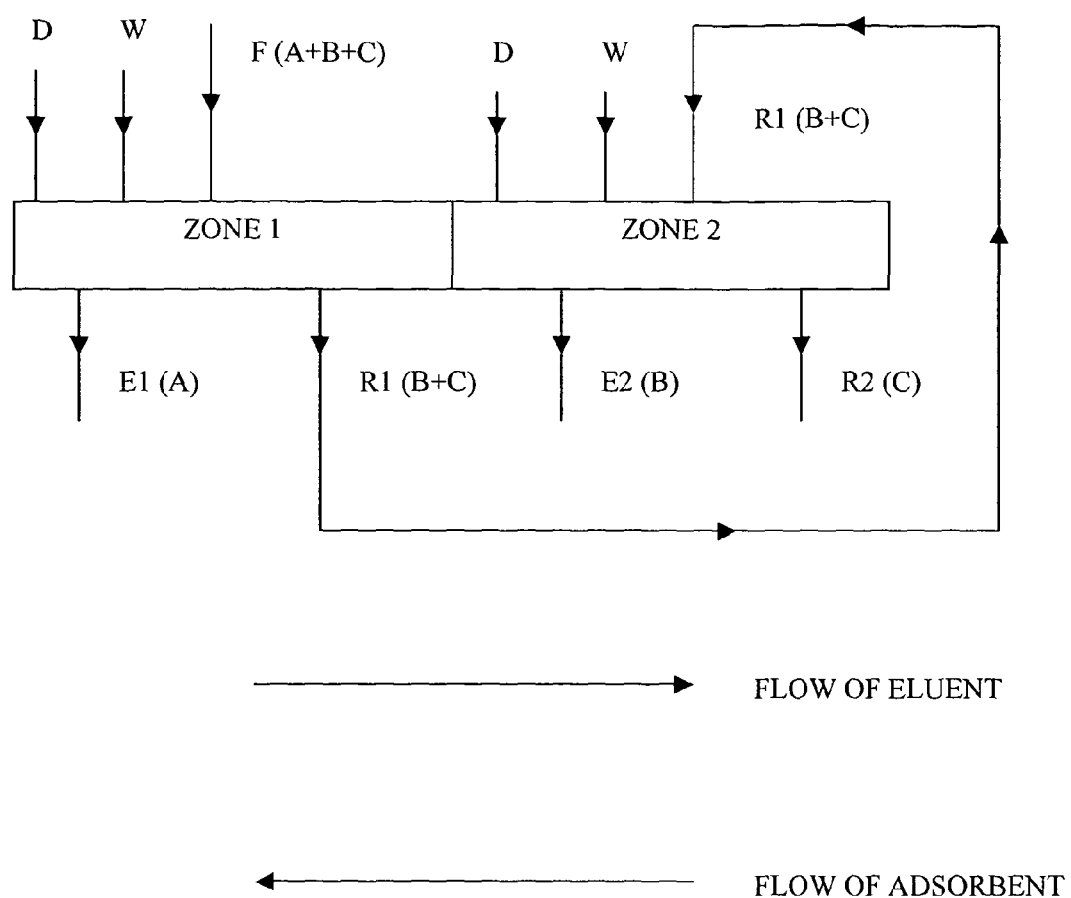
FIG. 4 illustrates in more detail the first preferred embodiment of the invention which is suitable for separating EPA from faster and slower running components (i.e. more polar and less polar impurities).

This embodiment is illustrated in more detail in FIG. 4. FIG. 4 is identical to FIG. 2, except that the points of introduction of the alcohol desorbent (D) and water (W) into each zone are shown. The alcohol desorbent (D) and water (W) together make up the eluent. The (D) phase is typically essentially pure alcohol, but may, in certain embodiments be an alcohol/water mixture comprising mainly alcohol. The (W) phase is typically essentially pure water, but may, in certain embodiments be an alcohol/water mixture comprising mainly water, for example a 98% water/2% methanol mixture.

Figure 6:
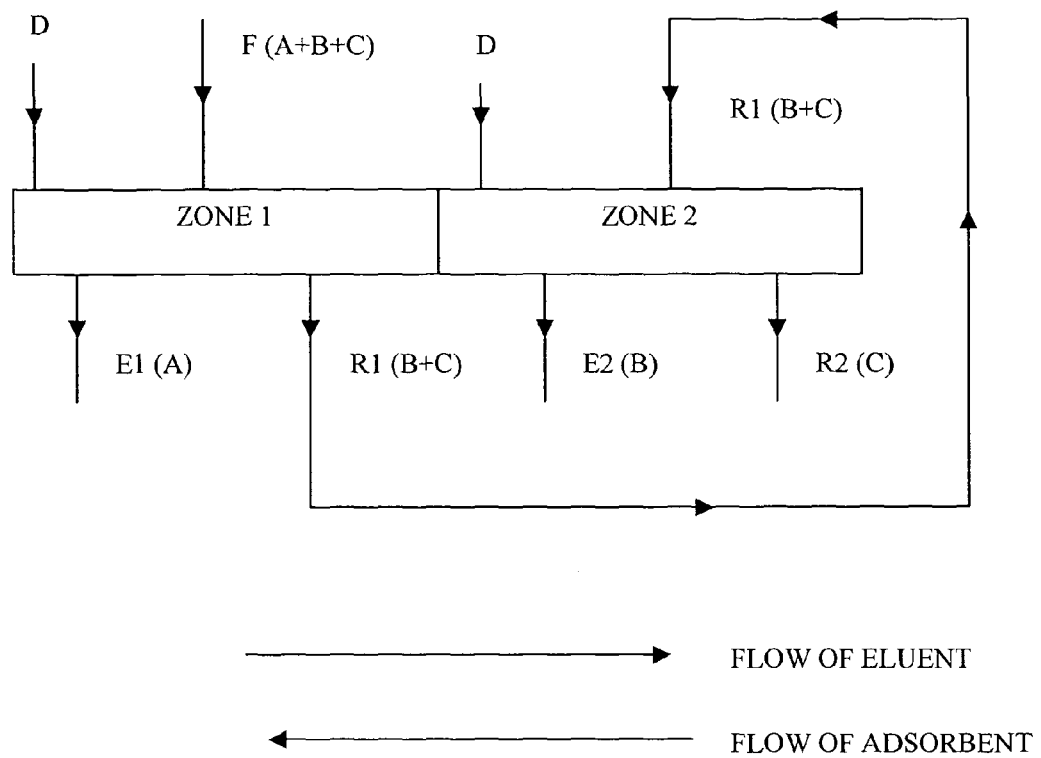
FIG. 6 illustrates in more detail an alternative method for the first preferred embodiment of the invention which is suitable for separating EPA from faster and slower running components (i.e. more polar and less polar impurities).

A further illustration of this particularly preferred embodiment is shown in FIG. 6. Here there is no separate water injection point, and instead an aqueous alcohol desorbent is injected at (D).

The separation into raffinate and extract stream can be aided by varying the desorbing power of the eluent within each zone. This can be achieved by introducing the alcohol (or alcohol rich) component of the eluent and the water (or water rich) component at different points in each zone. Thus, typically, the alcohol is introduced upstream of the extract take-off point and the water is introduced between the extract take-off point and the point of introduction of the feed into the zone, relative to the flow of eluent in the system. This is shown in FIG. 4.

Alternatively, the separation can be aided by varying the rates at which liquid collected via the extract and raffinate streams from the two zones is recycled back into the same zone.

Typically, in this particularly preferred embodiment, the rate at which liquid collected via the extract stream from the first zone is recycled back into the first zone is faster than the rate at which liquid collected via the extract stream from the second zone is recycled back into the second zone; or the water:alcohol ratio of the eluent in the first zone is lower than that in the second zone.

In this particularly preferred embodiment the first raffinate stream in the first zone is typically removed downstream of the point of introduction of the feed mixture into the first zone, with respect to the flow of eluent in the first zone.

In this particularly preferred embodiment, the first extract stream in the first zone is typically removed upstream of the point of introduction of the feed mixture into the first zone, with respect to the flow of eluent in the first zone.

In this particularly preferred embodiment, the second raffinate stream in the second zone is typically removed downstream of the point of introduction of the first raffinate stream into the second zone, with respect to the flow of eluent in the second zone.

In this particularly preferred embodiment, the second extract stream in the second zone is typically collected upstream of the point of introduction of the first raffinate stream into the second zone, with respect to the flow of eluent in the second zone.

Typically in this particularly preferred embodiment, the alcohol or aqueous alcohol is introduced into the first zone upstream of the point of removal of the first extract stream, with respect to the flow of eluent in the first zone.

Typically in this particularly preferred embodiment, when water is introduced into the first zone, the water is introduced into the first zone upstream of the point of introduction of the feed mixture but downstream of the point of removal of the first extract stream, with respect to the flow of eluent in the first zone.

Typically in this particularly preferred embodiment, the alcohol or aqueous alcohol is introduced into the second zone upstream of the point of removal of the second extract stream, with respect to the flow of eluent in the second zone.

Typically in this particularly preferred embodiment, when water is introduced into the second zone, the water is introduced into the second zone upstream of the point of introduction of the first raffinate stream but downstream of the point of removal of the second extract stream, with respect to the flow of eluent in the second zone.

In another particularly preferred embodiment, the apparatus has two zones, and the process comprises:
(i) introducing the feed mixture into the second zone, and removing a first raffinate stream depleted of the PUFA product and a first extract stream enriched in the PUFA product, and
(ii) introducing the first extract stream into the first zone, removing a second extract stream depleted of the PUFA product, and collecting a second raffinate stream to obtain the PUFA product.

This particularly preferred embodiment is suitable for purifying DHA from a feed mixture.

Figure 3:
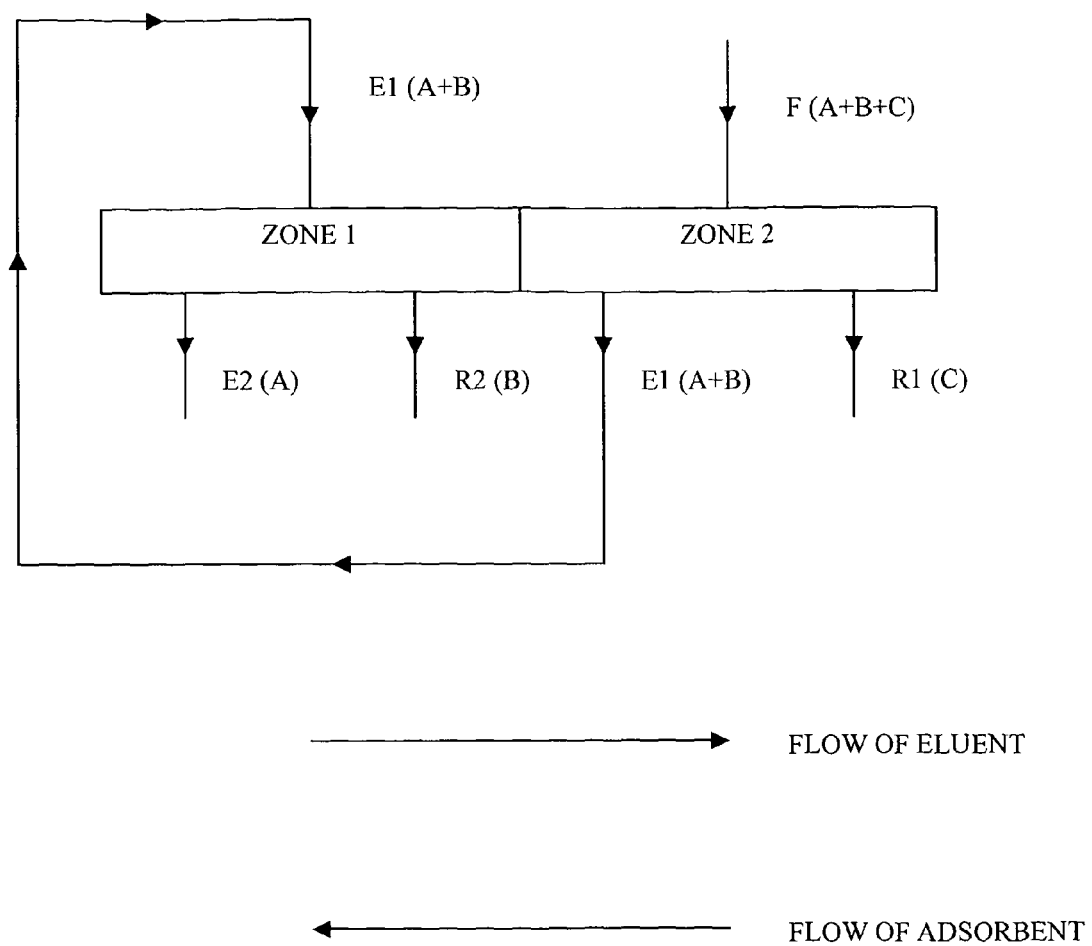
FIG. 3 illustrates a second preferred embodiment of the invention which is suitable for separating DHA from faster and slower running components (i.e. more polar and less polar impurities).

This embodiment is illustrated in FIG. 3. A feed mixture F comprising the PUFA product (B) and more polar (C) and less polar (A) components is introduced into the second zone. In the second zone, the more polar components (C) are removed as raffinate stream R1. The PUFA product (B) and less polar components (A) are collected as extract stream E1. Extract stream E1 is then introduced to the first zone. In the first zone, the less polar components (A) are removed as extract stream E2. The PUFA product (B) is collected as raffinate stream R2.

Figure 5:
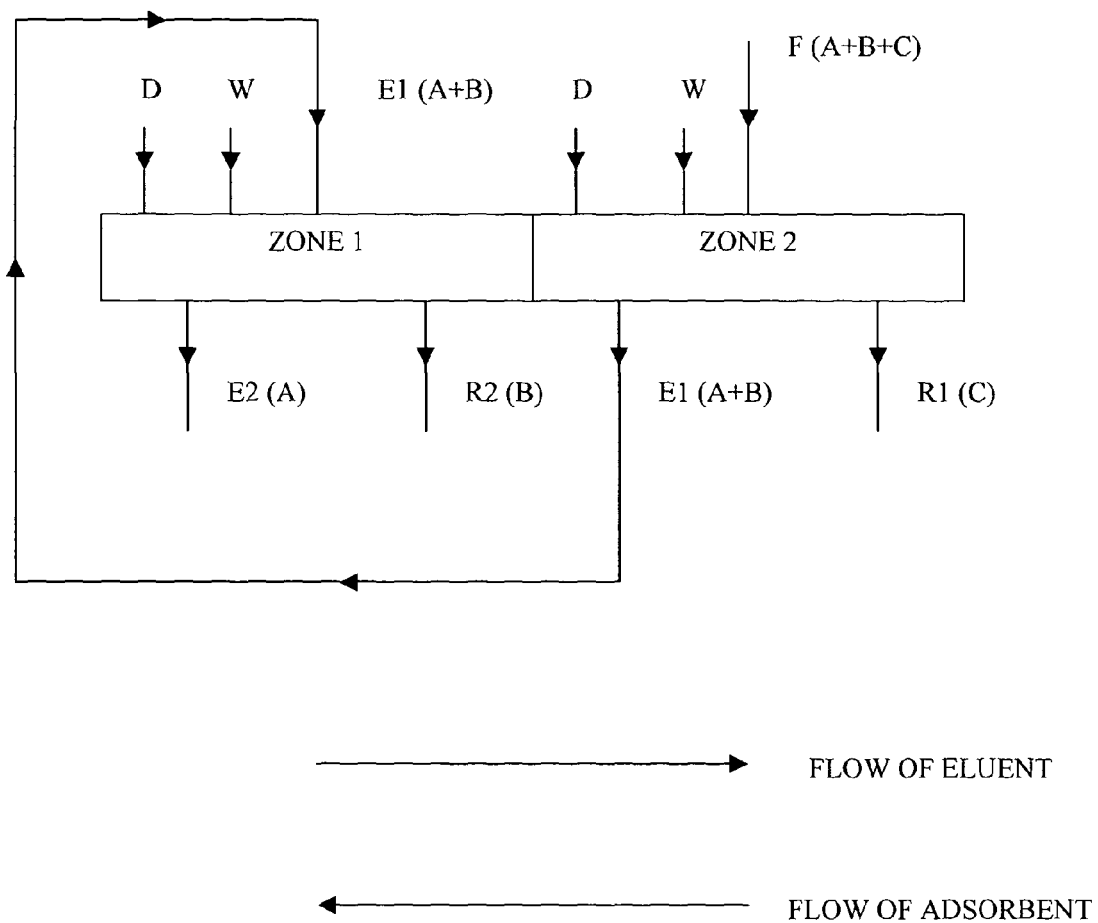
FIG. 5 illustrates in more detail the second preferred embodiment of the invention which is suitable for separating DHA from faster and slower running components (i.e. more polar and less polar impurities).

This embodiment is illustrated in more detail in FIG. 5. FIG. 5 is identical to FIG. 3, except that the points of introduction of the short chain alcohol desorbent (D) and water (W) into each zone are shown. As above, the (D) phase is typically essentially pure alcohol, but may, in certain embodiments be an alcohol/water mixture comprising mainly alcohol. The (W) phase is typically essentially pure water, but may, in certain embodiments be an alcohol/water mixture comprising mainly water, for example a 98% water/2% methanol mixture.

Figure 7:
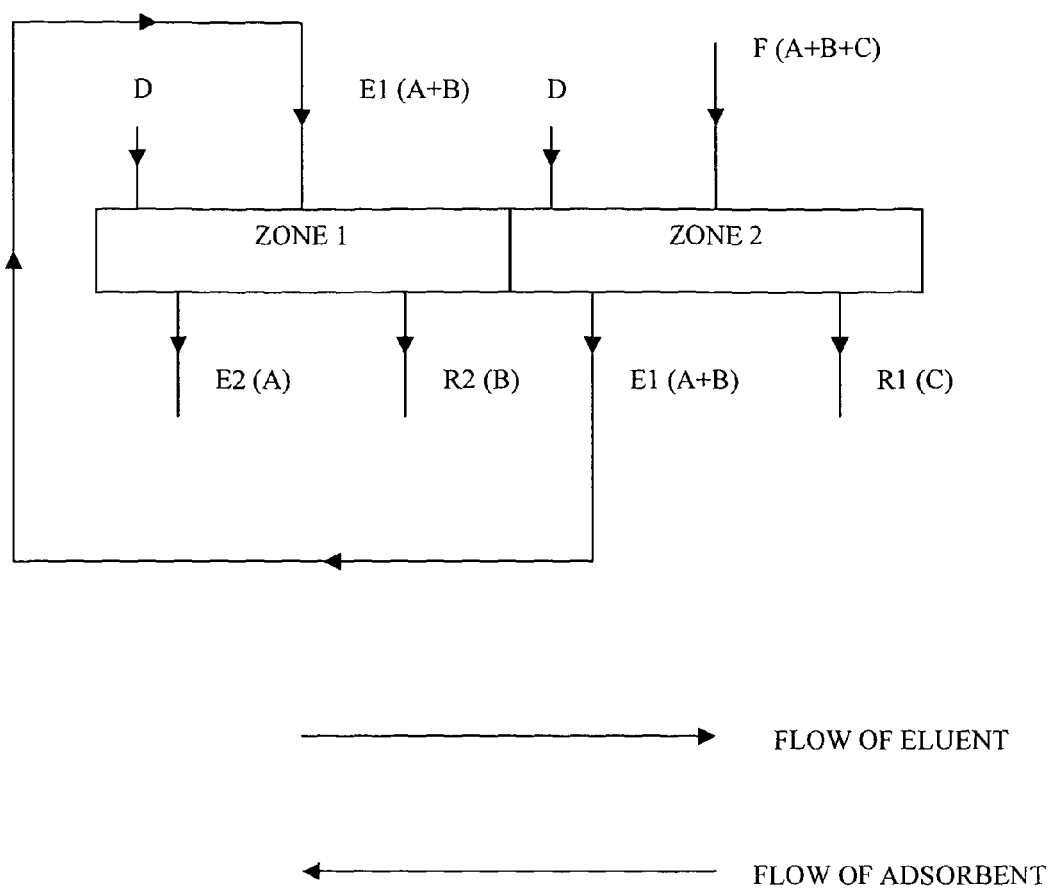
FIG. 7 illustrates in more detail an alternative method for the second preferred embodiment of the invention which is suitable for separating DHA from faster and slower running components (i.e. more polar and less polar impurities).

A further illustration of this particularly preferred embodiment is shown in FIG. 7. Here there is no separate water injection point, and instead an aqueous alcohol desorbent is injected at (D).

Typically in this embodiment, the rate at which liquid collected via the raffinate stream from the second zone is reintroduced into the second zone is faster than the rate at which liquid collected via the raffinate stream from the first zone is reintroduced into the first zone; or the water:alcohol ratio of the eluent in the first zone is lower than that in the second zone.

In this second particularly preferred embodiment, the first raffinate stream in the second zone is typically removed downstream of the point of introduction of the feed mixture into the second zone, with respect to the flow of eluent in the second zone.

In this second particularly preferred embodiment, the first extract stream in the second zone is typically collected upstream of the point of introduction of the feed mixture into the second zone, with respect to the flow of eluent in the second zone.

In this second particularly preferred embodiment, the second raffinate stream in the first zone is typically collected downstream of the point of introduction of the first extract stream into the first zone, with respect to the flow of eluent in the first zone.

In this second particularly preferred embodiment, the second extract stream in the first zone is typically removed upstream of the point of introduction of the first extract stream into the first zone, with respect to the flow of eluent in the first zone.

Typically in this second particularly preferred embodiment, the alcohol or aqueous alcohol is introduced into the second zone upstream of the point of removal of the first extract stream, with respect to the flow of eluent in the second zone.

Typically in this second particularly preferred embodiment, when water is introduced into the second zone, the water is introduced into the second zone upstream of the point of introduction of the feed mixture but downstream of the point of removal of the first extract stream, with respect to the flow of eluent in the second zone.

Typically in this second particularly preferred embodiment, the alcohol or aqueous alcohol is introduced into the first zone upstream of the point of removal of the second extract stream, with respect to the flow of eluent in the first zone.

Typically in this second particularly preferred embodiment, when water is introduced into the first zone, the water is introduced into the first zone upstream of the point of introduction of the first raffinate stream but downstream of the point of removal of the second extract stream, with respect to the flow of eluent in the first zone.

In a preferred embodiment of the invention, the simulated or actual moving bed chromatography apparatus consists of fifteen chromatographic columns. These are referred to as columns 1 to 15. The fifteen columns are arranged in series so that the bottom of column 1 is linked to the top of column 2, the bottom of column 2 is linked to the top of column 3 etc. This may optionally be via a holding container, with a recycle stream into the next column. The flow of eluent through the system is from column 1 to column 2 to column 3 etc. The flow of adsorbent through the system is from column 15 to column 14 to column 13 etc.

In a most preferred embodiment, the first zone typically consists of eight adjacent columns, columns 1 to 8, which are connected as discussed above. In this most preferred embodiment, the second zone typically consists of seven columns, columns 9 to 15, which are connected as discussed above. For the avoidance of doubt, the bottom of column 8 in the first zone is linked to the top of column 9 in the second zone.

Figure 8:
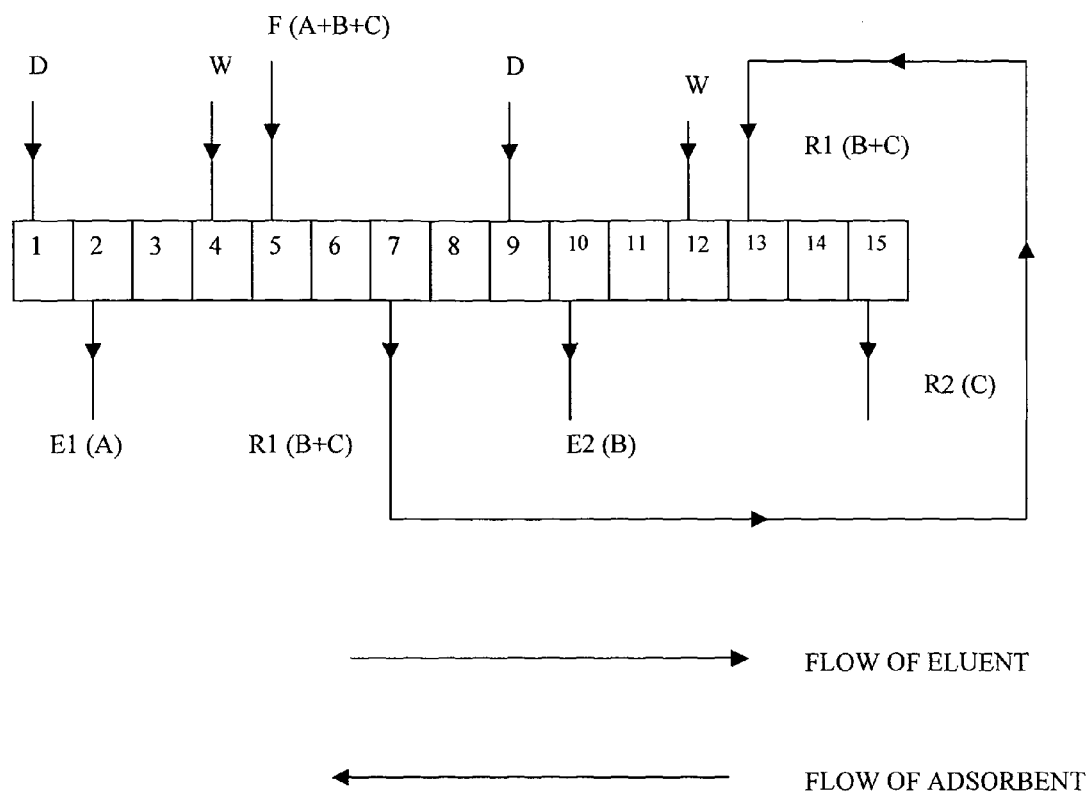
FIG. 8 illustrates a particularly preferred embodiment of the invention for purifying EPA from faster and slower running components (i.e. more polar and less polar impurities).

A most preferred embodiment is illustrated in FIG. 8. A feed mixture F comprising the PUFA product (B) and more polar (C) and less polar (A) components is introduced into the top of column 5 in the first zone. Alcohol desorbent is introduced into the top of column 1 in the first zone. Water is introduced into the top of column 4 in the first zone. In the first zone, the less polar components (A) are removed as extract stream E1 from the bottom of column 2. The PUFA product (B) and more polar components (C) are removed as raffinate stream R1 from the bottom of column 7. Raffinate stream R1 is then introduced into the second zone at the top of column 13. Alcohol desorbent is introduced into the top of column 9 in the second zone. Water is introduced into the top of column 12 in the second zone. In the second zone, the more polar components (C) are removed as raffinate stream R2 at the bottom of column 15. The PUFA product (B) is collected as extract stream E2 at the bottom of column 10.

In this most preferred embodiment, alcohol is typically introduced into the top of column 1 in the first zone.

In this most preferred embodiment, water is typically introduced into the top of column 4 in the first zone.

In this most preferred embodiment, alcohol is typically introduced into the top of column 9 in the second zone.

In this most preferred embodiment, alcohol is typically introduced into the top of column 12 in the second zone.

In this most preferred embodiment, the feed stream is typically introduced into the top of column 5 in the first zone.

In this most preferred embodiment, a first raffinate stream is typically collected from the bottom of column 7 in the first zone and introduced into the top of column 13 in the second zone. The first raffinate stream may optionally be collected in a container before being introduced into column 13.

In this most preferred embodiment, a first extract stream is typically removed from the bottom of column 2 in the first zone. The first extract stream may optionally be collected in a container and reintroduced into the top of column 3 in the first zone.

In this most preferred embodiment, a second raffinate stream is typically removed from the bottom of column 15 in the second zone.

In this most preferred embodiment, a second extract stream is typically collected from the bottom of column 10 in the second zone. This second extract stream typically contains the purified PUFA product. The second extract stream may optionally be collected in a container and reintroduced into the top of column 11 in the second zone.

Typically, in this most preferred embodiment, the water:alcohol ratio in the first zone is lower than the water:alcohol ratio in the second zone.

Figure 9:
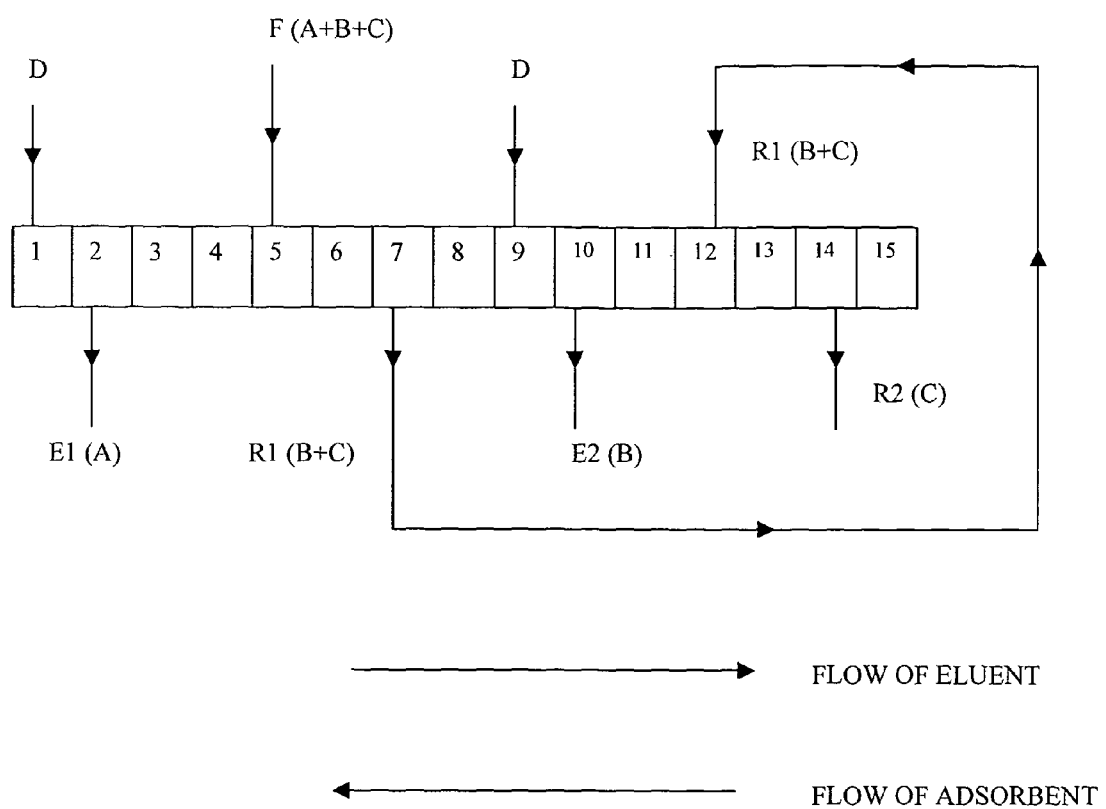
FIG. 9 illustrates an alternative method for a particularly preferred embodiment of the invention for purifying EPA from faster and slower running components (i.e. more polar and less polar impurities).

A further most preferred embodiment is illustrated in FIG. 9. A feed mixture F comprising the PUFA product (B) and more polar (C) and less polar (A) components is introduced into the top of column 5 in the first zone. Aqueous alcohol desorbent is introduced into the top of column 1 in the first zone. In the first zone, the less polar components (A) are removed as extract stream E1 from the bottom of column 2. The PUFA product (B) and more polar components (C) are removed as raffinate stream R1 from the bottom of column 7. Raffinate stream R1 is then introduced into the second zone at the top of column 12. Aqueous alcohol desorbent is introduced into the top of column 9 in the second zone. In the second zone, the more polar components (C) are removed as raffinate stream R2 at the bottom of column 14. The PUFA product (B) is collected as extract stream E2 at the bottom of column 10.

In this most preferred embodiment, aqueous alcohol is typically introduced into the top of column 1 in the first zone.

In this most preferred embodiment, aqueous alcohol is typically introduced into the top of column 9 in the second zone.

In this most preferred embodiment, the feed stream is typically introduced into the top of column 5 in the first zone.

In this most preferred embodiment, a first raffinate stream is typically collected from the bottom of column 7 in the first zone and introduced into the top of column 12 in the second zone. The first raffinate stream may optionally be collected in a container before being introduced into column 12.

In this most preferred embodiment, a first extract stream is typically removed from the bottom of column 2 in the first zone. The first extract stream may optionally be collected in a container and a portion reintroduced into the top of column 3 in the first zone. The rate of recycle of liquid collected via the extract stream from the first zone back into the first zone is the rate at which liquid is pumped from this container into the top of column 3.

In this most preferred embodiment, a second raffinate stream is typically removed from the bottom of column 14 in the second zone.

In this most preferred embodiment, a second extract stream is typically collected from the bottom of column 10 in the second zone. This second extract stream typically contains the purified PUFA product. The second extract stream may optionally be collected in a container and a portion reintroduced into the top of column 11 in the second zone. The rate of recycle of liquid collected via the extract stream from the second zone back into the second zone is the rate at which liquid is pumped from this container into the top of column 11.

In this most preferred embodiment, the rate at which liquid collected via the extract stream from the first zone is recycled back into the first zone is typically faster than the rate at which liquid collected via the extract stream from the second zone is recycled back into the second zone.

In this most preferred embodiment, the aqueous alcohol eluent is substantially the same in each zone.

In a further preferred embodiment of the invention, the simulated or actual moving bed chromatography apparatus consists of nineteen chromatographic columns. These are referred to as columns 1 to 19. The fifteen columns are arranged in series so that the bottom of column 1 is linked to the top of column 2, the bottom of column 2 is linked to the top of column 3 etc. The flow of eluent through the system is from column 1 to column 2 to column 3 etc. The flow of adsorbent through the system is from column 19 to column 18 to column 17 etc.

In this embodiment, the first zone typically consists of ten adjacent columns, columns 1 to 10, which are connected as discussed above. The second zone typically consists of eight columns, columns 11 to 19, which are connected as discussed above.

Figure 10:
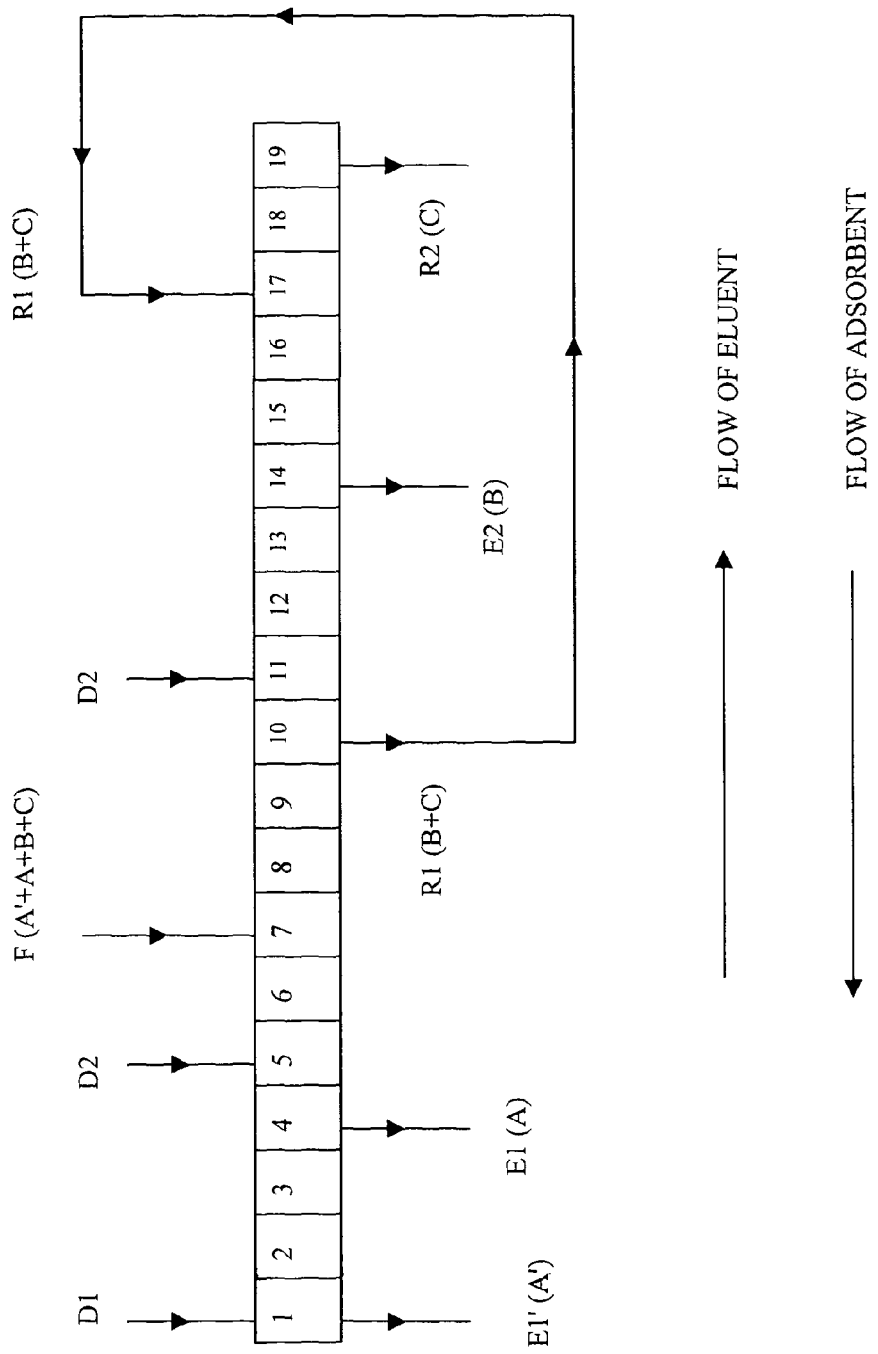
FIG. 10 illustrates a particularly preferred embodiment of the invention for purifying EPA from faster and slower running components (i.e. more polar and less polar impurities).

This further preferred embodiment is illustrated in FIG. 10. A feed mixture F comprising the PUFA product (B) and more polar (C) and less polar (A and A') components is introduced into the top of column 7 in the first zone. A first desorbent (D1) comprising 100% alcohol is introduced into the top of column 1 in the first zone. A second desorbent (D2) comprising a water/alcohol mixture (preferably 2% methanol and 98% water) is introduced into the top of column 5 in the first zone. In the first zone, less polar components (A') and (A) are removed as extract streams E1' and E1 from the bottoms of columns 1 and 4, respectively. The PUFA product (B) and more polar components (C) are removed as raffinate stream R1 from the bottom of column 10. Raffinate stream R1 is then introduced into the second zone at the top of column 17. A second desorbent (D2) comprising a water/alcohol mixture (preferably 2% methanol and 98% water) is introduced into the top of column 11 in the second zone. In the second zone, the more polar components (C) are removed as raffinate stream R2 at the bottom of column 19. The PUFA product (B) is collected as extract stream E2 at the bottom of column 14.

In this preferred embodiment, alcohol is typically introduced into the top of column 1 in the first zone.

In this preferred embodiment, a 2% MeOH/98% water mixture is typically introduced into the top of column 5 in the first zone.

In this preferred embodiment, a 2% MeOH/98% water mixture is typically introduced into the top of column 11 in the second zone.

In this preferred embodiment, the feed stream is typically introduced into the top of column 7 in the first zone.

In this preferred embodiment, a first raffinate stream is typically collected from the bottom of column 10 in the first zone and introduced into the top of column 17 in the second zone. The first raffinate stream may optionally be collected in a container before being introduced into column 17.

In this preferred embodiment, extract streams are typically removed from the bottoms of columns 1 and 4 in the first zone. The extract stream collected from the bottom or column 4 may optionally be collected in a container and reintroduced into the top of column 5 in the first zone.

In this preferred embodiment, a second raffinate stream is typically removed from the bottom of column 19 in the second zone.

In this preferred embodiment, a second extract stream is typically collected from the bottom of column 14 in the second zone. This second extract stream typically contains the purified PUFA product. The second extract stream may optionally be collected in a container and reintroduced into the top of column 15 in the second zone.

Typically, in this most preferred embodiment, the water:alcohol ratio in the first zone is lower than the water:alcohol ratio in the second zone.

The process of the invention allows much higher purities of PUFA product to be achieved than have been possible with conventional chromatographic techniques. PUFA products produced by the process of the invention also have particularly advantageous impurity profiles, which are quite different from those observed in oils prepared by known techniques. The present invention therefore also relates to compositions comprising a PUFA product, for example one obtainable by the process of the present invention.

Thus, in one embodiment the present invention also provides a composition comprising a PUFA product, wherein the PUFA product is EPA, the PUFA product is present in an amount greater than 93 wt %, and the total content of ω-6 polyunsaturated fatty acids is up to 0.40 wt %.

As used herein, the wt % of a component is relative to the total weight of the composition.

The PUFA product and ω-6 PUFAs are optionally in the form of their alkyl esters, typically ethyl esters. Preferably, the EPA PUFA product is in the form of its ethyl ester.

Typically, in this embodiment the EPA PUFA product is present in an amount greater than 94 wt %, preferably greater than 95 wt %, more preferably greater than 96 wt %, even more preferably greater than 97 wt %, and most preferably greater than 98 wt %.

The total content of ω-6 polyunsaturated fatty acids in this embodiment is up to 0.40 wt %. Thus, typically, the composition comprises an amount of ω-6 polyunsaturated fatty acids in up to this amount. Typically, the total content of ω-6 polyunsaturated fatty acids is up to 0.35 wt %, preferably up to 0.3 wt %, more preferably up to 0.25 wt %, and most preferably up to 0.22 wt %. Typically, the total content of ω-6 polyunsaturated fatty acids is 0.05 wt % or greater, preferably 0.1 wt % or greater.

Typically, in this embodiment the content of arachidonic acid is up to 0.25 wt %, preferably up to 0.24 wt %, more preferably up to 0.23 wt %, and most preferably up to 0.22 wt %. Thus, typically, the composition comprises an amount of arachidonic acid in up to these amounts. Typically, the total content of arachidonic acid is 0.05 wt % or greater, preferably 0.1 wt % or greater.

Typically, in this embodiment the total content of ω-3 polyunsaturated fatty acids is greater than 97 wt %, preferably greater than 97.5 wt %, more preferably greater than 97.9 wt %. In certain embodiments, the total content of ω-3 polyunsaturated fatty acids is greater than 99 wt %.

Typically, in this embodiment the total content of DHA is up to 1 wt %, preferably up to 0.6 wt %, more preferably up to 0.3 wt %, most preferably up to 0.2 wt %. Thus, typically, the composition comprises an amount of DHA in up to these amounts. Typically, the total content of DHA is 0.05 wt % or greater, preferably 0.1 wt % or greater.

Typically, in this embodiment the total content of DHA is up to 0.2 wt %, preferably up to 0.175 wt %, more preferably up to 0.16 wt %. Thus, typically, the composition comprises an amount of DHA in up to these amounts. Typically, the total content of DHA is 0.05 wt % or greater, preferably 0.1 wt % or greater.

Typically, in this embodiment the total content of α-linolenic acid is up to 1 wt %, preferably up to 0.6 wt %, more preferably up to 0.3 wt %. Thus, typically, the composition comprises an amount of α-linolenic acid in up to these amounts. Typically, the total content of α-linolenic acid is 0.05 wt % or greater, preferably 0.1 wt % or greater.

Typically, in this embodiment the total content of α-linolenic acid is up to 0.35 wt %, preferably up to 0.3 wt %, more preferably up to 0.29 wt %. Thus, typically, the composition comprises an amount of α-linolenic acid in up to these amounts. Typically, the total content of α-linolenic acid is 0.05 wt % or greater, preferably 0.1 wt % or greater.

Typically, in this embodiment the total content of stearidonic acid is up to 1 wt %, preferably up to 0.6 wt %, more preferably up to 0.3 wt %. Thus, typically, the composition comprises an amount of stearidonic acid in up to these amounts. Typically, the total content of stearidonic acid is 0.05 wt % or greater, preferably 0.1 wt % or greater.

Typically, in this embodiment the total content of stearidonic acid is up to 0.4 wt %, preferably up to 0.35 wt %, more preferably up to 0.34 wt %. Thus, typically, the composition comprises an amount of stearidonic acid in up to these amounts.

Typically, the total content of stearidonic acid is 0.05 wt % or greater, preferably 0.1 wt % or greater.

Typically, in this embodiment the total content of eicosatetraenoic acid is up to 1 wt %, preferably up to 0.75 wt %, more preferably up to 0.5 wt %. Thus, typically, the composition comprises an amount of eicosatetraenoic acid in up to these amounts. Typically, the total content of eicosatetraenoic acid is 0.05 wt % or greater, preferably 0.1 wt % or greater.

Typically, in this embodiment the total content of eicosatetraenoic acid is up to 0.5 wt %, preferably up to 0.475 wt %, more preferably up to 0.46 wt %. Thus, typically, the composition comprises an amount of eicosatetraenoic acid in up to these amounts. Typically, the total content of eicosatetraenoic acid is 0.05 wt % or greater, preferably 0.1 wt % or greater.

Typically, in this embodiment the total content of docosapentaenoic acid is up to 1 wt %, preferably up to 0.6 wt %, more preferably up to 0.3 wt %. Thus, typically, the composition comprises an amount of docosapentaenoic acid in up to these amounts. Typically, the total content of docosapentaenoic acid is 0.05 wt % or greater, preferably 0.1 wt % or greater.

Typically, in this embodiment the total content of docosapentaenoic acid is up to 0.4 wt %, preferably up to 0.35 wt %, more preferably up to 0.33 wt %. Thus, typically, the composition comprises an amount of docosapentaenoic acid in up to these amounts. Typically, the total content of docosapentaenoic acid is 0.05 wt % or greater, preferably 0.1 wt % or greater.

In this embodiment, the composition preferably comprises greater than 96.5 wt % EPA, up to 1 wt % DHA, up to 1 wt % α-linolenic acid, up to 1 wt % stearidonic acid, up to 1 wt % eicosatetraenoic acid, up to 1 wt % docosapentaenoic acid, and up to 0.25 wt % arachidonic acid.

In this embodiment, the composition preferably comprises greater than 96.5 wt % EPA, up to 0.2 wt % DHA, up to 0.3 wt % α-linolenic acid, up to 0.4 wt % stearidonic acid, up to 0.5 wt % eicosatetraenoic acid, up to 0.35 wt % docosapentaenoic acid, and up to 0.25 wt % arachidonic acid.

In this embodiment, the composition more preferably comprises from 96.5 to 99 wt % EPA, up to 0.6 wt % DHA, up to 0.6 wt % α-linolenic acid, from 0.15 to 0.6 wt % stearidonic acid, from 0.1 to 0.75 wt % eicosatetraenoic acid, up to 0.6 wt % docosapentaenoic acid, and up to 0.6 wt % arachidonic acid.

In this embodiment, the composition more preferably comprises from 96.5 to 99 wt % EPA, up to 0.2 wt % DHA, up to 0.3 wt % α-linolenic acid, from 0.15 to 0.4 wt % stearidonic acid, from 0.1 to 0.5 wt % eicosatetraenoic acid, up to 0.35 wt % docosapentaenoic acid, and up to 0.25 wt % arachidonic acid.

In this embodiment, the composition most preferably comprises from 98 to 99 wt % EPA, from 0.1 to 0.3 wt % DHA, from 0.3 to 0.35 wt % stearidonic acid, from 0.1 to 0.3 wt % eicosatetraenoic acid, and from 0.3 to 0.35 wt % docosapentaenoic acid.

In this embodiment, the composition most preferably comprises from 96.5 to 99 wt % EPA, from 0.1 to 0.5 wt % DHA, from 0.1 to 0.5 wt % stearidonic acid, from 0.1 to 0.5 wt % eicosatetraenoic acid, from 0.1 to 0.5 wt % docosapentaenoic acid, and from 0.1 to 0.3 wt % arachidonic acid.

In this embodiment, the composition most preferably comprises from 98 to 99 wt % EPA, from 0.1 to 0.2 wt % DHA, from 0.3 to 0.35 wt % stearidonic acid, from 0.1 to 0.2 wt % eicosatetraenoic acid, and from 0.3 to 0.35 wt % docosapentaenoic acid.

In this embodiment, the composition most preferably comprises from 96.5 to 97.5 wt % EPA, from 0.25 to 0.35 wt % α-linolenic acid, from 0.18 to 0.24 wt % stearidonic acid, from 0.4 to 0.46 wt % eicosatetraenoic acid, and from 0.15 to 0.25 wt % arachidonic acid.

Typically, in this embodiment, the content of isomeric impurities is up to 1.5 wt %. Typically, the content of isomeric impurities is up to 1 wt %, preferably up to 0.5 wt %, more preferably up to 0.25 wt %, even more preferably up to 0.25 wt %, and most preferably up to 0.1 wt %.

In a further embodiment, the present invention also provides a composition comprising a PUFA product, wherein the PUFA product is a mixture of EPA and DHA, wherein (i) the total content of EPA and DHA is 80 wt % or greater, (ii) the content of EPA is from 41 to 60 wt % and the content of DHA is from 16 to 48 wt %, and (iii) the total content of ω-3 polyunsaturated fatty acids is 94 wt % or greater and/or the total content of ω-6 polyunsaturated fatty acids is up to 4 wt %.

The PUFA product, ω-3 and ω-6 PUFAs are optionally in the form of their alkyl esters, typically ethyl esters. Preferably, the EPA/DHA PUFA product is in the form of its ethyl esters.

Thus, in this further embodiment the composition is typically a composition comprising a PUFA product, wherein the PUFA product is a mixture of EPA and DHA, wherein (i) the total content of EPA and DHA is 80 wt % or greater, (ii) the content of EPA is from 41 to 60 wt % and the content of DHA is from 16 to 48 wt %, and (iii) the total content of ω-3 polyunsaturated fatty acids is 94 wt % or greater.

Alternatively, in this further embodiment the composition is a composition comprising a PUFA product, wherein the PUFA product is a mixture of EPA and DHA, wherein (i) the total content of EPA and DHA is 80 wt % or greater, (ii) the content of EPA is from 41 to 60 wt % and the content of DHA is from 16 to 48 wt %, and (iii) the total content of ω-6 polyunsaturated fatty acids is up to 4 wt %.

Typically, in this further embodiment the total content of EPA and DHA is 82 wt % or greater, preferably 83 wt % or greater, more preferably 84 wt % or greater, even more preferably 85 wt % or greater, and most preferably 86 wt % or greater.

Typically, in this further embodiment the content of EPA is from 41 to 60 wt %, preferably from 45 to 60 wt %, more preferably from 47 to 60 wt %, even more preferably from 47 to 57 wt %, and most preferably from 50 to 55 wt %.

Typically, in this further embodiment the content of DHA is from 16 to 48 wt %, preferably from 20 to 45 wt %, more preferably from 25 to 42 wt %, even more preferably from 28 to 38 wt %, and most preferably from 30 to 35 wt %.

Typically, in this further embodiment the total content of ω-3 polyunsaturated fatty acids is 94 wt % or greater, preferably 95 wt % or greater, more preferably 96 wt % or greater, and most preferably 97 wt % or greater.

Typically, in this further embodiment the total content of α-linolenic acid is up to 0.4 wt %, preferably up to 0.35 wt %, more preferably up to 0.31 wt %. Thus, typically, the composition comprises an amount of α-linolenic acid in up to these amounts. Typically, the total content of α-linolenic acid is 0.05 wt % or greater, preferably 0.1 wt % or greater, more preferably 0.2 wt % or greater, and even preferably from 0.2 to 0.4 wt %.

Typically, in this further embodiment the total content of stearidonic acid is up to 1.9 wt %, preferably up to 1.5 wt %, more preferably up to 1.25 wt %. Thus, typically, the composition comprises an amount of stearidonic acid in up to these amounts. Typically, the total content of stearidonic acid is 0.05 wt % or greater, preferably 0.1 wt % or greater.

Typically, in this further embodiment the total content of eicosatetraenoic acid is up to 2.0 wt %, preferably up to 1.9 wt %. Thus, typically, the composition comprises an amount of eicosatetraenoic acid in up to these amounts. Typically, the total content of eicosatetraenoic acid is 0.05 wt % or greater, preferably 0.1 wt % or greater, more preferably 1.0 wt % or greater, and even more preferably from 1.0 to 1.9 wt %.

Typically, in this further embodiment the total content of eicosapentaenoic acid is up to 3.0 wt %, preferably up to 2.75 wt %. Thus, typically, the composition comprises an amount of eicosapentaenoic acid in up to these amounts. Typically, the total content of eicosapentaenoic acid is 0.05 wt % or greater, preferably 0.1 wt % or greater, more preferably 2 wt % or greater, and even more preferably from 2 to 2.75 wt %.

Typically, in this further embodiment the total content of docosapentaenoic acid is up to 6 wt %, preferably up to 5.5 wt %, more preferably up to 5.25 wt %. Thus, typically, the composition comprises an amount of docosapentaenoic acid in up to these amounts. Typically, the total content of docosapentaenoic acid is 0.05 wt % or greater, preferably 0.1 wt % or greater, more preferably 4 wt % or greater, and even more preferably from 4 to 5.25 wt %.

The total content of ω-6 polyunsaturated fatty acids in this further embodiment is typically up to 4 wt %. Thus, typically, the composition comprises an amount of ω-6 polyunsaturated fatty acids up to these amounts. Typically, the total content of ω-6 polyunsaturated fatty acids is up to 3.75 wt %, preferably up to 3.5 wt %, more preferably up to 3.25 wt %, even more preferably up to 3 wt %, most preferably up to 2.85 wt %. Typically, the total content of ω-6 polyunsaturated fatty acids is 0.05 wt % or greater, preferably 0.1 wt % or greater.

Typically, in this further embodiment the total content of linoleic acid is up to 0.5 wt %, preferably up to 0.4 wt %, more preferably up to 0.25 wt %. Thus, typically, the composition comprises an amount of linoleic acid in up to these amounts. Typically, the total content of linoleic acid is 0.05 wt % or greater, preferably 0.1 wt % or greater, more preferably 0.15 wt % or greater, and even more preferably from 0.15 to 0.25 wt %.

Typically, in this further embodiment the total content of gamma-linolenic acid is up to 0.19 wt %, preferably up to 0.15 wt %, more preferably up to 0.1 wt %. Thus, typically, the composition comprises an amount of gamma-linolenic acid in up to these amounts. Typically, the total content of gamma-linolenic acid is 0.05 wt % or greater, preferably 0.1 wt % or greater.

Typically, in this further embodiment the total content of dihommo-gamma-linolenic acid is up to 0.1 wt %. Thus, typically, the composition comprises an amount of dihommo-gamma-linolenic acid in up to these amounts. Typically, the total content of dihommo-gamma-linolenic acid is 0.05 wt % or greater.

Typically, in this further embodiment the total content of arachidonic acid is up to 2.5 wt %, preferably up to 2.25 wt %, more preferably up to 2.1 wt %. Thus, typically, the composition comprises an amount of arachidonic acid in up to these amounts. Typically, the total content of arachidonic acid is 0.05 wt % or greater, preferably 0.1 wt % or greater.

Typically, in this further embodiment the total content of adrenic acid is up to 0.1 wt %. Thus, typically, the composition comprises an amount of adrenic acid in up to this amount. Typically, the total content of adrenic acid is 0.05 wt % or greater.

Typically, in this further embodiment the total content of docosapentaenoic ($\omega$-6) acid is up to 0.9 wt %, preferably up to 0.75 wt %. More preferably up to 0.65 wt %. Thus, typically, the composition comprises an amount of docosapentaenoic ($\omega$-6) acid in up to these amounts. Typically, the total content of docosapentaenoic ($\omega$-6) acid is 0.05 wt % or greater, preferably 0.1 wt % or greater.

In this further embodiment, the composition preferably comprises from 50 to 55 wt % EPA, from 30 to 35 wt % DHA, up to 0.4 wt % $\alpha$-linolenic acid, up to 1.25 wt % stearidonic acid, up to 1.9 wt % eicosatetraenoic acid, up to 2.75 wt % eicosapentaenoic acid, up to 5.25 wt % docosapentaenoic acid, up to 0.25 wt % linoleic acid, up to 0.1 wt % gamma-linolenic acid, up to 0.1 wt % dihommo-gamma-linolenic acid, up to 2.1 wt % arachidonic acid, up to 0.1 wt % adrenic acid, and up to 0.75 wt % docosapentaenoic ($\omega$-6) acid.

In this further embodiment, the composition more preferably comprises from 50 to 55 wt % EPA, from 30 to 35 wt % DHA, from 0.2 to 0.4 wt % $\alpha$-linolenic acid, up to 1.25 wt % stearidonic acid, from 1.0 to 1.9 wt % eicosatetraenoic acid, from 2 to 2.75 wt % eicosapentaenoic acid, from 4 to 5.25 wt % docosapentaenoic acid, from 0.15 to 0.25 wt % linoleic acid, up to 0.1 wt % gamma-linolenic acid, up to 0.1 wt % dihommo-gamma-linolenic acid, up to 2.1 wt % arachidonic acid, up to 0.1 wt % adrenic acid, and up to 0.75 wt % docosapentaenoic ($\omega$-6) acid.

Typically, in this further embodiment, the content of isomeric impurities is up to 1.5 wt %. Typically, the content of isomeric impurities is up to 1 wt %, preferably up to 0.5 wt %, more preferably up to 0.25 wt %, even more preferably up to 0.25 wt %, and most preferably up to 0.1 wt %.

The inventors have also surprisingly found that oils can be produced with a reduced amount of environmental pollutants, compared with known oils. Thus, in a still further embodiment the present invention also provides a composition comprising a PUFA product, as defined herein, wherein (a) the total amount of polyaromatic hydrocarbons in the composition is up to 0.89 µg/kg, (b) the total amount of dioxins, furans, dibenzeno-para-dioxins and polychlorinated dibenzofurans is up to 0.35 pg/g (c) the total amount of polychlorinated biphenyls is up to 0.0035 mg/kg, and/or (d) the total amount of dioxins, furans, dibenzeno-para-dioxins, polychlorinated dibenzofurans and dioxin-like polychlorinated biphenyls is up to 1 pg/g.

Typically, the present invention provides a composition comprising a PUFA product, as defined herein, wherein (a) the total amount of polyaromatic hydrocarbons in the composition is up to 0.89 µg/kg, (b) the total amount of dioxins, furans, dibenzeno-para-dioxins and polychlorinated dibenzofurans is up to 0.35 pg/g, and/or (d) the total amount of dioxins, furans and dioxin-like polychlorinated biphenyls is up to 1 pg/g.

The total amount of polyaromatic hydrocarbons in this still further embodiment in the composition is up to 0.89 µg/kg. Thus, typically, the composition comprises an amount of polyaromatic hydrocarbons up to this amount. Typically, the total amount of polyaromatic hydrocarbons in the composition is up to 0.85 µg/kg, preferably up to 0.8 µg/kg, more preferably up to 0.7 µg/kg, even more preferably up to 0.6 µg/kg, still more preferably up to 0.5 µg/kg, yet more preferably up to 0.4 µg/kg, yet more preferably up to 0.3 mg/kg, yet more preferably up to 0.2 µg/kg, yet more preferably up to 0.1 µg/kg, and most preferably up to 0.05 µg/kg.

Typical polyaromatic hydrocarbons are well known to one skilled in the art and include acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(ah)anthracene, fluoranthene, fluorine, indeno(1,2,3-cd)pyrene, phenanthrene, pyrene, coronene, corannulene, tetracene, naphthalene, pentacene, triphenylene, and ovalene. Typically, the amounts referred to above refer to the content of benzo[a]pyrene.

The total amount of dioxins, furans, dibenzeno-para-dioxins and polychlorinated dibenzofurans in this still further embodiment is up to 0.35 pg/g. Thus, typically, the composition comprises an amount of dioxins, furans, dibenzeno-para-dioxins and polychlorinated dibenzofurans up to this amount. Typically, the total amount of dioxins, furans, dibenzeno-para-dioxins and polychlorinated dibenzofurans is up to 0.325 pg/g, preferably up to 0.3 pg/g, more preferably up to 0.275 pg/g, even more preferably up to 0.25 pg/g, still more preferably up to 0.225 pg/g, yet more preferably up to 0.2 pg/g, and most preferably up to 0.185 pg/g. These amounts are expressed in World Health Organisation (WHO) toxic equivalents using WHO-toxic equivalent factors (TEFs). WHO-toxic equivalent factors are well known to the person skilled in the art.

Dioxins, furans, dibenzeno-para-dioxins (PCDDs) and polychlorinated dibenzofurans (PCDFs) are well known to the skilled person. Typically, these are as defined in Community regulations (EC) No. 1881/2006 and 1883/2006 the entirety of which is incorporated herein by reference.

The PCDDs, PCDFs and Dioxin-like PCBs defined in Community regulations (EC) No. 1881/2006 and 1883/2006 together with their TEF values are as follows.

| Congener | TEF value |
| --- | --- |
| Dibenzo-p-dioxins (PCDDs) | |
| 2,3,7,8-TCDD | 1 |
| 1,2,3,7,8-PeCDD | 1 |
| 1,2,3,4,7,8-HxCDD | 0.1 |

-continued

| Congener | TEF value |
| --- | --- |
| 1,2,3,6,7,8-HxCDD | 0.1 |
| 1,2,3,7,8,9-HxCDD | 0.1 |
| 1,2,3,4,6,7,8-HpCDD | 0.01 |
| OCDD | 0.0001 |
| Dibenzofurans (PCDFs) | |
| 2,3,7,8-TCDF | 0.1 |
| 1,2,3,7,8-PeCDF | 0.05 |
| 2,3,4,7,8-PeCDF | 0.5 |
| 1,2,3,4,7,8-HxCDF | 0.1 |
| 1,2,3,6,7,8-HxCDF | 0.1 |
| 1,2,3,7,8,9-HxCDF | 0.1 |
| 2,3,4,6,7,8-HxCDF | 0.1 |
| 1,2,3,4,6,7,8-HpCDF | 0.01 |
| 1,2,3,4,7,8,9-HpCDF | 0.01 |
| OCDF | 0.0001 |
| Dioxin-like PCBs: Non-ortho PCBs + Mono-ortho PCBs | |
| Non-ortho PCBs | |
| PCB 77 | 0.0001 |
| PCB 81 | 0.0001 |
| PCB 126 | 0.1 |
| PCB 169 | 0.01 |
| Mono-ortho PCBs | |
| PCB 105 | 0.0001 |
| PCB 114 | 0.0005 |
| PCB 118 | 0.0001 |
| PCB 123 | 0.0001 |
| PCB 156 | 0.0005 |
| PCB 157 | 0.0005 |
| PCB 167 | 0.00001 |
| PCB 189 | 0.0001 |

Abbreviations used:
'T' = tetra;
'Pe' = penta;
'Hx' = hexa;
'Hp' = hepta;
'O' = octa;
'CDD' = chlorodibenzodioxin;
'CDF' = chlorodibenzofuran;
'CB' = chlorobiphenyl.

Typically, the quantity of PCDDs, PCDFs and Dioxin-like PCBs is determined according to the method set out in Community regulations (EC) No. 1881/2006 and 1883/2006.

The total amount of polychlorinated biphenyls in this still further embodiment is up to 0.0035 mg/kg. Thus, typically, the composition comprises an amount of polychlorinated biphenyls up to this amount. Typically, the total amount of polychlorinated biphenyls is up to 0.003 mg/kg, preferably up to 0.0025 mg/kg, more preferably up to 0.002 mg/kg, even more preferably up to 0.0015 mg/kg, still more preferably up to 0.001 mg/kg, yet more preferably up to 0.00075 mg/kg, and most preferably up to 0.0007 mg/kg.

Polychlorobiphenyls (PCBs) are well known in the art and includes biphenyl, monochlorobiphenyl, dichlorobiphenyl, trichlorobiphenyl, tetrachlorobiphenyl, pentachlorobiphenyl, hexachlorobiphenyl, heptachlorobiphenyl, octachlorobiphenyl, nonachlorobiphenyl, and decachlorobiphenyl.

The total amount of dioxins, furans, dibenzeno-para-dioxins, polychlorinated dibenzofurans and dioxin-like polychlorinated biphenyls in this still further embodiment is up to 1 pg/g. Thus, typically, the composition comprises an amount of dioxins, furans, dibenzeno-para-dioxins, polychlorinated dibenzofurans and dioxin-like polychlorinated biphenyls in up to this amount. Typically, the total amount of dioxins, furans, dibenzeno-para-dioxins, polychlorinated dibenzofurans and dioxin-like polychlorinated biphenyls is up to 0.75 pg/g, preferably up to 0.5 pg/g, more preferably up to 0.45 pg/g, even more preferably up to 0.4 pg/g, still more preferably up to 0.35 pg/g, and most preferably up to 0.3 pg/g.

Dioxins, furans, dibenzeno-para-dioxins (PCDDs), polychlorinated dibenzofurans (PCDFs) and dioxin-like polychlorinated biphenyls are well known to the skilled person. Typically, these are as defined in Community regulation (EC) No. 1881/2006 and 1883/2006 the entirety of which is incorporated herein by reference.

The PCDDs, PCDFs and Dioxin-like PCBs defined in Community regulation (EC) No. 1881/2006 and 1883/2006 together with their TEF values are as defined above.

In this still further embodiment, preferably (a) the total amount of polyaromatic hydrocarbons in the composition is up to 0.05 μg/kg, (b), the total amount of dioxins, furans, dibenzeno-para-dioxins and polychlorinated dibenzofurans is up to 0.2 pg/g (c) the total amount of polychlorinated biphenyls is up to 0.0015 mg/kg, and/or (d) the total amount of dioxins, furans, dibenzeno-para-dioxins and polychlorinated dibenzofurans and dioxin-like polychlorinated biphenyls is up to 0.3 pg/g.

In this still further embodiment, preferably (a) the total amount of polyaromatic hydrocarbons in the composition is up to 0.05 μg/kg, (b), the total amount of dioxins, furans, dibenzeno-para-dioxins and polychlorinated dibenzofurans is up to 0.2 pg/g and/or (d) the total amount of dioxins, furans, dibenzeno-para-dioxins and polychlorinated dibenzofurans and dioxin-like polychlorinated biphenyls is up to 0.3 pg/g.

In this still further embodiment, more preferably (a) the total amount of polyaromatic hydrocarbons in the composition is up to 0.05 (b), the total amount of dioxins, furans, dibenzeno-para-dioxins and polychlorinated dibenzofurans is up to 0.2 pg/g (c) the total amount of polychlorinated biphenyls is up to 0.0015 mg/kg, and (d) the total amount of dioxins, furans, dibenzeno-para-dioxins and polychlorinated dibenzofurans and dioxin-like polychlorinated biphenyls is up to 0.3 pg/g.

In this still further embodiment, more preferably (a) the total amount of polyaromatic hydrocarbons in the composition is up to 0.05 μg/kg, (b), the total amount of dioxins, furans, dibenzeno-para-dioxins and polychlorinated dibenzofurans is up to 0.2 pg/g, and (d) the total amount of dioxins, furans, dibenzeno-para-dioxins and polychlorinated dibenzofurans and dioxin-like polychlorinated biphenyls is up to 0.3 pg/g.

Typically, in this still further embodiment, the content of isomeric impurities is up to 1.5 wt %. Typically, the content of isomeric impurities is up to 1 wt %, preferably up to 0.5 wt %, more preferably up to 0.25 wt %, even more preferably up to 0.25 wt %, and most preferably up to 0.1 wt %.

The inventors have also found that oils of high purity can be produced which avoid the problems of isomerization, peroxidation and oligomerization associated with distilled oils. The quantity of isomeric impurities present in a PUFA product of the present invention will depend on the amount of isomeric impurities present in the feed mixture. Crucially, though, the amount of isomeric impurities is not increased by the process of the present invention, unlike distillation. Thus, the limit of the content of isomers in the PUFA product is the isomeric content of the starting material. If the starting material has no isomers present, then the resultant PUFA product will also be substantially free of isomers. This advantage is not observed in distillation.

Thus, in one embodiment, the chromatographic separation process of the present invention does not substantially increase the amount of isomeric impurities in the PUFA product relative to the amount of isomeric impurities present in the feed mixture. "Substantially increase" is typically understood to mean increase by 10 wt % or less, preferably 5 wt % or less, more preferably 3 wt % or less, even more preferably 1 wt % or less, yet more preferably 0.5 wt % or less, and most preferably 0.1 wt % or less.

Thus, in a yet further embodiment, the present invention also provides a composition comprising a PUFA product, wherein the content of isomeric impurities is up to 1.5 wt %. Typically, the composition contains an amount of isomeric impurities up to this amount. Typically, the content of isomeric impurities is up to 1 wt %, preferably up to 0.5 wt %, more preferably up to 0.25 wt %, and most preferably up to 0.1 wt %. Isomerisation is particularly problematic in the preparation of high purity DHA by distillation, due to the higher temperatures required for separation. Typically, the PUFA product is DHA, optionally in the form of its ethyl ester. Typically the composition comprises greater than 85 wt % PUFA product, preferably greater than 90 wt %, more preferably greater than 92.5 wt %, most preferably greater than 95 wt %. Preferably, the composition contain comprises greater than 85 wt % DHA, optionally in the form of its ethyl ester, preferably greater than 90 wt %, more preferably greater than 92.5 wt %, most preferably greater than 95 wt %. In this embodiment, the composition typically comprises as PUFA product DHA, optionally in the form of its ethyl ester, in an amount greater than 95 wt %, wherein the content of isomeric impurities is up to 1 wt %, preferably up to 0.5 wt %, more preferably up to 0.25 wt %, and most preferably up to 0.1 wt %

The improved process of the invention allows much higher purities of PUFA product to be achieved efficiently, as both the more and less polar impurities can be removed in a single process.

The PUFA product of the present invention typically has a purity of greater than 80 weight %, preferably greater than 85 weight %, more preferably greater than 90 weight %, even more preferably greater than 95 weight %, yet more preferably greater than 97 weight %, and most preferably greater than 99 weight %. When the PUFA product is a single PUFA or derivative thereof, the concentrations above refer to the concentration of that PUFA or derivative. When the PUFA product is a mixture of two or more PUFAs or derivatives thereof, for example two, the concentrations above refer to the combined concentration of the PUFAs, or derivatives thereof.

The method of the present invention also avoids the problems of isomerization, peroxidation and oligomerization associated with distilled oils. The PUFA product of the present invention typically has a content of isomeric impurities of less than 5 weight %, preferably less than 3 weight %, and more preferably less than 1 weight %. As mentioned above, the isomeric impurities include PUFA isomers, peroxidation and oligomerization products. PUFA isomers include positional and/or geometric isomers. Examples of positional and/or geometric isomers of EPA include 17E-EPA, 5E-EPA, 5E,8E-EPA, 8E,11E-EPA, 5E,14E-EPA, and 5E,8E,11E,17E-EPA. Such isomers are discussed in more detail in Wijesundera, R. C., et al, Journal of the American Oil Chemists Society, 1989, vol. 66, no. 12, 1822-1830, the entirety of which is incorporated herein by reference.

In practice, the process of the present invention will generally be controlled by a computer. The present invention therefore also provides a computer program for controlling a chromatographic apparatus as defined herein, the computer program containing code means that when executed instruct the apparatus to carry out the process of the invention.

The following Examples illustrate the invention.

EXAMPLES

Example 1

A fish oil derived feedstock (55 weight % EPA EE, 5 weight % DHA EE) is fractionated using an actual moving bed chromatography system using bonded C18 silica gel (particle size 300 µm) as stationary phase and aqueous methanol as eluent according to the system schematically illustrated in FIG. 8. 15 columns (diameter: 76.29 mm, length: 914.40 mm) are connected in series as shown in FIG. 8.

Figure 11:
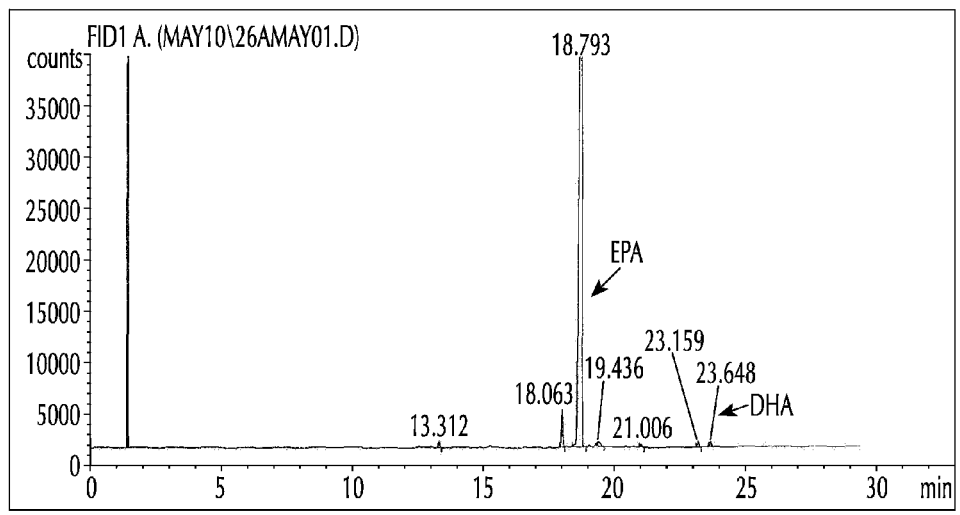
FIG. 11 shows a GC analysis of an EPA product produced in accordance with the invention.
Figure 12:
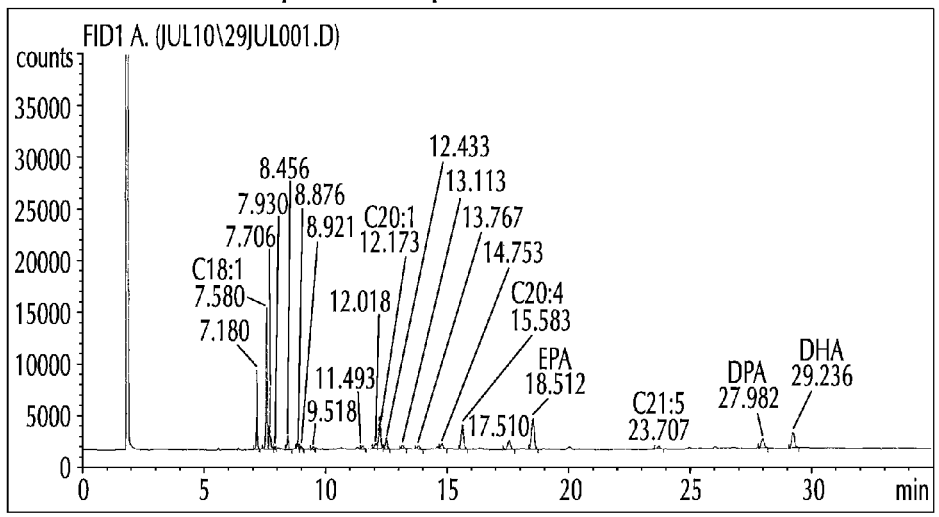
FIG. 12 shows GC FAMES traces of first extract and raffinate streams obtained in accordance with the invention.
Figure 12:
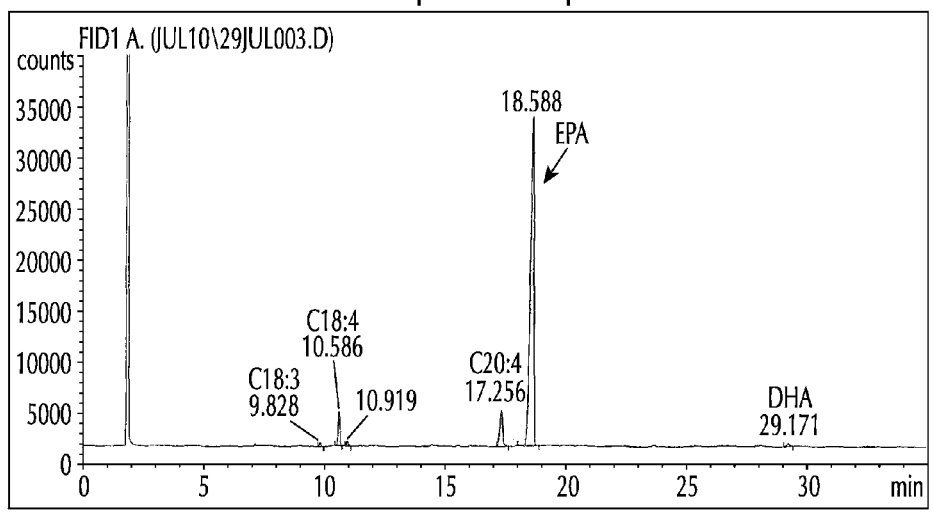

The operating parameters and flowrates are as follows for eight different cases. For the conditions below, EPA EE is produced at a high level of purity (85 to 98% by GC FAMES). GC FAMES traces of the zone 1 extract and raffinate, and of the zone 2 extract and raffinate are shown as FIGS. 11 and 12 respectively.

Example 1a

Step time: 750 secs
Cycle time: 200 mins
Feedstock (F) feed rate: 70 ml/min
Desorbent (D) feed rate: 850 ml/min
Extract rate: 425 ml/min
Raffinate rate: 495 ml/min Example 1b Step time: 250 secs
Cycle time: 66.67 mins
Feedstock (F) feed rate: 210 ml/min
Desorbent (D) feed rate: 2550 ml/min
Extract rate: 1275 ml/min
Raffinate rate: 1485 ml/min Example 1c Step time: 500 secs
Cycle time: 133.33 mins
Feedstock (F) feed rate: 25 ml/min
Desorbent feed rate (D1) in first zone: 2050 ml/min
Extract container accumulation rate (E1) in first zone: 1125 ml/min
Extract recycle rate (D1-E1) in first zone: 925 ml/min
Raffinate rate (R1) in first zone: 950 ml/min
Desorbent feed rate (D2) in second zone: 1700 ml/min
Extract container accumulation rate (E2) in second zone: 900 ml/min
Extract recycle rate (D2-E2) in second zone: 800 ml/min
Raffinate rate (R2) in second zone: 800 ml/min Example 1d Step time: 250 secs
Cycle time: 66.67 mins
Feedstock (F) feed rate: 50 ml/min
Desorbent feed rate (D1) in first zone: 4125 ml/min
Extract container accumulation rate (E1) in first zone: 2250 ml/min
Extract recycle rate (D1-E1) in first zone: 1875 ml/min
Raffinate rate (R1) in first zone: 1925 ml/min
Desorbent feed rate (D2) in second zone: 3375 ml/min Extract container accumulation rate (E2) in second zone: 1800 ml/min
Extract recycle rate (D2−E2) in second zone: 1575 ml/min
Raffinate rate (R2) in second zone: 1575 ml/min Example 1e Step time: 500 secs
Cycle time: 133.33 mins
Feedstock (F) feed rate: 50 ml/min
Desorbent feed rate (D1) in first zone: 4000 ml/min
Extract container accumulation rate (E1) in first zone: 2250 ml/min
Extract recycle rate (D1−E1) in first zone: 1750 ml/min
Raffinate rate (R1) in first zone: 1800 ml/min
Desorbent feed rate (D2) in second zone: 3200 ml/min
Net extract accumulation rate (E2) in second zone: 1750 ml/min
Extract recycle rate (D2−E2) in second zone: 1450 ml/min
Raffinate rate (R2) in second zone: 1450 ml/min Example 1f Step time: 250 secs
Cycle time: 66.67 mins
Feedstock (F) feed rate: 100 ml/min
Desorbent feed rate (D1) in first zone: 4050 ml/min
Extract container accumulation rate (E1) in first zone: 2100 ml/min
Extract recycle rate (D1−E1) in first zone: 1950 ml/min
Raffinate rate (R1) in first zone: 2050 ml/min
Desorbent feed rate (D2) in second zone: 3300 ml/min
Net extract accumulation rate (E2) in second zone: 1700 ml/min
Extract recycle rate (D2−E2) in second zone: 1600 ml/min
Raffinate rate (R2) in second zone: 1600 ml/min Example 1g Step time: 500 secs
Cycle time: 133.33 mins
Feedstock (F) feed rate: 25 ml/min
Desorbent feed rate (D1) in first zone: 1275 ml/min
Extract container accumulation rate (E1) in first zone: 750 ml/min
Extract recycle rate (D1−E1) in first zone: 550 ml/min
Raffinate rate (R1) in first zone: 575 ml/min
Desorbent feed rate (D2) in second zone: 1275 ml/min
Net extract accumulation rate (E2) in second zone: 950 ml/min
Extract recycle rate (D2−E2) in second zone: 325 ml/min
Raffinate rate (R2) in second zone: 325 ml/min Example 1h Step time: 250 secs
Cycle time: 66.67 mins
Feedstock (F) feed rate: 50 ml/min
Desorbent feed rate (D1) in first zone: 2550 ml/min
Extract container accumulation rate (E1) in first zone: 1500 ml/min
Extract recycle rate (D1−E1) in first zone: 950 ml/min
Raffinate rate (R1) in first zone: 1000 ml/min
Desorbent feed rate (D2) in second zone: 2000 ml/min
Net extract accumulation rate (E2) in second zone: 900 ml/min
Extract recycle rate (D2−E2) in second zone: 600 ml/min
Raffinate rate (R2) in second zone: 600 ml/min Example 2

A fish oil derived feedstock comprising eicosatetraenoic acid ethyl ester (ETA EE), EPA EE, isomers thereof and DHA EE was fractionated using an actual moving bed chromatography system using bonded C18 silica gel (particle size 40-60 µm) as stationary phase and aqueous methanol as eluent according to the system schematically illustrated in FIG. 10. 19 columns (diameter: 10 mm, length: 250 mm) are connected in series as shown in FIG. 10.

The operating parameters and flowrates are as follows.
Cycle time: 600 secs
Feedstock (F) feed rate: 0.5 ml/min
Desorbent (D1, 100% methanol) feed rate into the first zone: 6 ml/min
Desorbent (D2, 99% methanol/1% water) feed rate into the first zone: 6 ml/min
Extract (E1') rate from the first zone: 3 ml/min
Extract (E1) rate from the first zone: 1.9 ml/min
Raffinate (R1) rate from the first zone: 4.6 ml/min
Desorbent (D2, 97% methanol/3% water) feed rate into the second zone: 6 ml/min
Extract (E2) rate from the second zone: 2.4 ml/min
Raffinate (R2) rate from the second zone: 4.6 ml/min Again, EPA EE was produced at a high level of purity (greater than 90 weight %, greater than 95 weight %, greater than 98 weight %).

Example 3

A fish oil derived feedstock (55 weight % EPA EE, 5 weight % DHA EE) was fractionated using an actual moving bed chromatography system using bonded C18 silica gel (particle size 300 µm, particle porosity 150 angstroms) as stationary phase and aqueous methanol as eluent according to the system schematically illustrated in FIG. 8. 15 columns (diameter: 10 mm, length: 250 mm) are connected in series as shown in FIG. 8.

Figure 13:
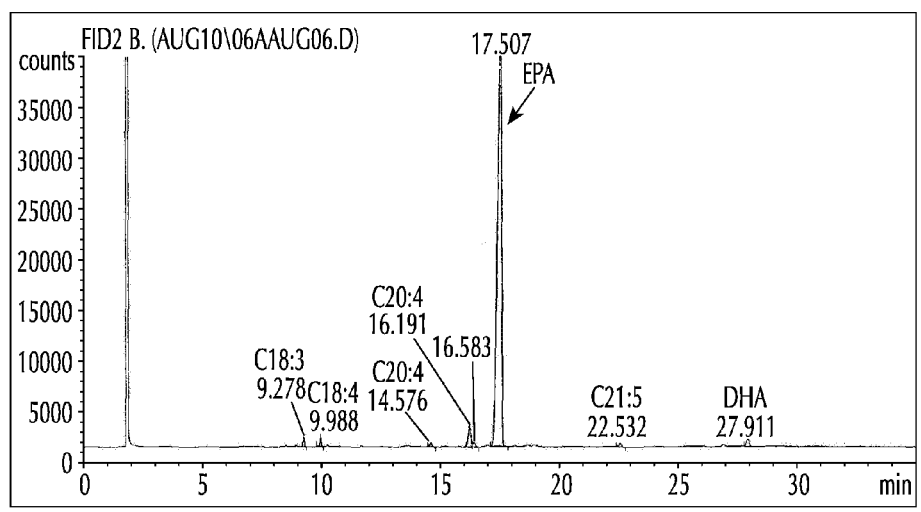
FIG. 13 shows GC FAMES traces of second extract and raffinate streams obtained in accordance with the invention.
Figure 13:
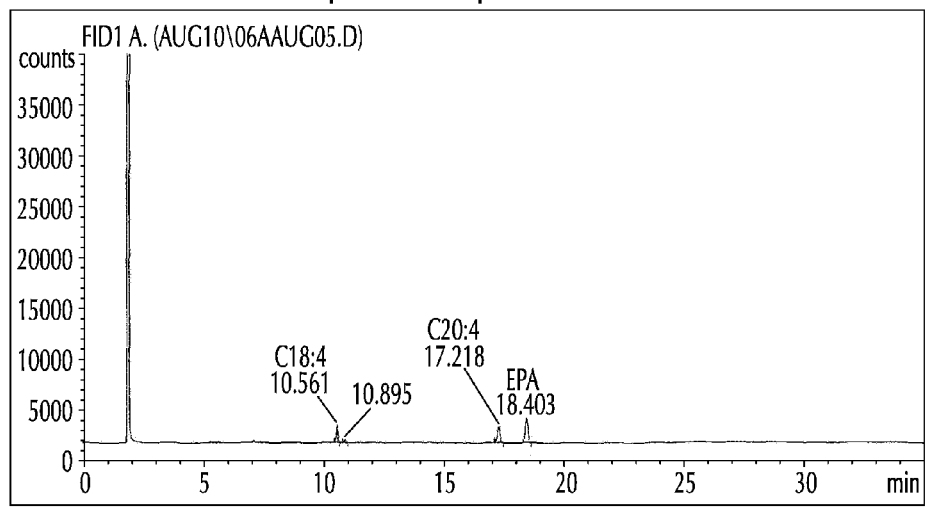

The operating parameters and flowrates are as follows.
Cycle time: 380 secs
Feedstock (F) feed rate: 0.5 ml/min
Desorbent (D, 98.5% methanol/1.5% water) feed rate into the first zone: 9 ml/min
Water rich phase (W; 85% methanol/15% water) feed rate into the first zone: 3.1 ml/min
Extract (E1) rate from the first zone: 4 ml/min
Raffinate (R1) rate from the first zone: 8.6 ml/min
Desorbent (D, 97% methanol/3% water) feed rate into the second zone: 10.8 ml/min
Water rich phase (W, 85% methanol/15% water) feed rate into the second zone: 3.1 ml/min
Extract (E2) rate from the second zone: 4.1 ml/min
Raffinate (R2) rate from the second zone: 10.3 ml/min EPA EE was produced at a high level of purity (>95% purity). A GC trace of the product is shown as FIG. 13

Example 4

A fish oil derived feedstock (70 weight % DHA EE, 7 weight % EPA EE) is fractionated using an actual moving bed chromatography system using bonded C18 silica gel (particle size 300 µm) as stationary phase and aqueous methanol as eluent according to the system schematically illustrated in FIG. 8. 15 columns (diameter: 76.29 mm, length: 914.40 mm) are connected in series as shown in FIG. 8.

The operating parameters and flowrates are as follows.
Step time: 600 secs
Cycle time: 160 mins
Feedstock (F) feed rate: 25 ml/min
Desorbent feed rate (D1) in first zone: 2062.5 ml/min
Extract rate (E1) in first zone: 900 ml/min
Raffinate rate (R1) in first zone: 1187.5 ml/min
Desorbent feed rate (D2) in second zone: 1500 ml/min
Extract rate (E2) in second zone: 450 ml/min
Raffinate rate (R2) in second zone: 1050 ml/min DHA EE is produced at a high level of purity (>97% by GC FAMES). A GC FAMES trace of the zone 2 extract is shown as FIG. 14.

Example 5

A fish oil derived feedstock (33 weight % EPA EE, 22 weight % DHA EE) is fractionated using an actual moving bed chromatography system using bonded C18 silica gel (particle size 300 μm) as stationary phase and aqueous methanol as eluent according to the system schematically illustrated in FIG. 8. 15 columns (diameter: 76.29 mm, length: 914.40 mm) are connected in series as shown in FIG. 8.

The operating parameters and flowrates are as follows.
Step time: 380 secs
Cycle time: 101.33 mins
Feedstock (F) feed rate: 40 ml/min
Desorbent feed rate (D1) in first zone: 1950 ml/min
Extract rate (E1) in first zone: 825 ml/min
Raffinate rate (R1) in first zone: 1165 ml/min
Desorbent feed rate (D2) in second zone: 1425 ml/min
Extract rate (E2) in second zone: 787.5 ml/min
Raffinate rate (R2) in second zone: 637.5 ml/min A mixture of EPA EE and DHA EE is produced at a high level of purity (>80% total EPA EE and DHA EE).

Example 6

An experiment was carried out to compare the amount of environmental pollutants present in two PUFA products according to the present invention with similar oils prepared by distillation. The pollutant profiles of the oils are shown in Table 1 below.

Example 7

An experiment was carried out to determine the amount of isomeric impurities present in an oil prepared according to the present invention compared with an equivalent oil prepared by distillation.

Figure 14:
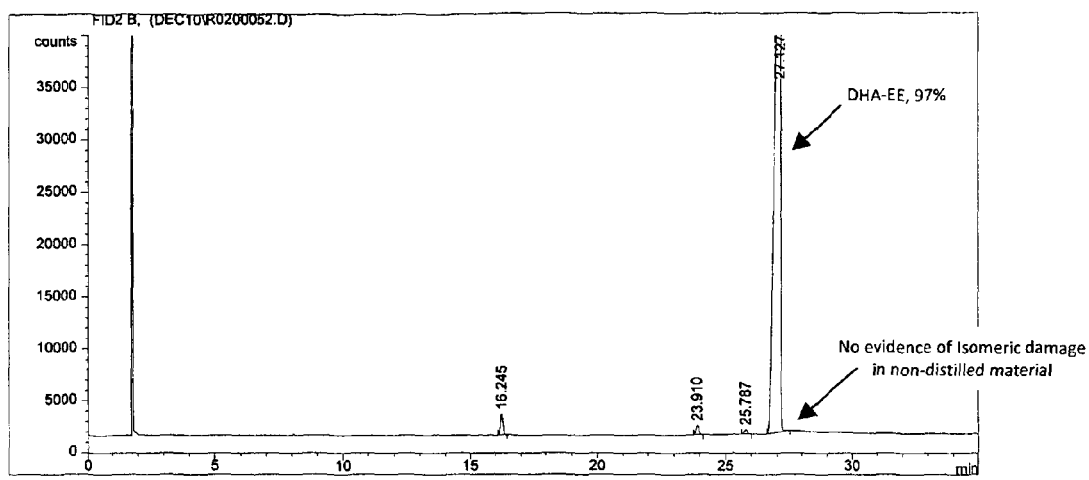
FIG. 14 shows a GC FAMES trace of a DHA product produced in accordance with the invention.

A GC trace of the DHA-rich oil prepared in accordance with the invention is shown as FIG. 14. There is no evidence of isomeric impurities in the GC trace.

Figure 15:
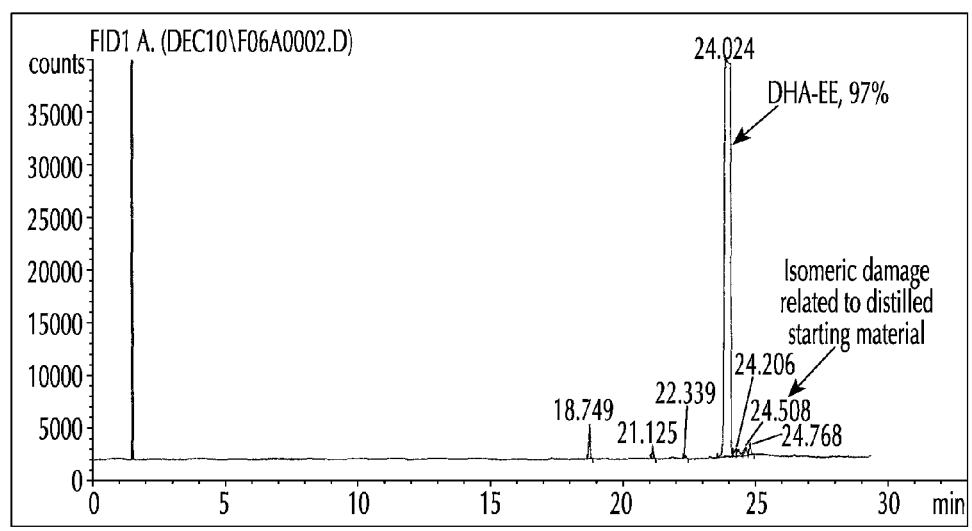
FIG. 15 shows a GC FAMES trace of a DHA product produced by distillation.

A GC trace of the oil prepared by distillation is shown as FIG. 15. The four peaks with longer elution times than the DHA peak correspond to DHA isomers. From the GC trace it can be seen that the oil prepared by distillation contains about 1.5 wt % of isomeric impurities.

Example 8

Two EPA-rich products of the process of the present invention were compared with EPA-rich oils produced by distillation. The wt % analysis of their component PUFAs is shown below.

| Fatty Acid | PUFA product according to the invention [1] | PUFA product according to the invention [2] | Distilled oil [1] | Distilled oil [2] |
|---|---|---|---|---|
| EPA (C20:5n-3) | 98.33 | 97.04 | 98.09 | 98.14 |
| DHA (C22:6n-3) | 0.15 | <LOD | 0.34 | <LOD |
| C18:3 n-3 | <LOD | 0.28 | 0.24 | <LOD |
| C18:4 n-3 | 0.33 | 0.20 | 0.14 | 0.26 |
| C20:4 n-3 | 0.14 | 0.45 | 0.18 | 0.46 |
| C21:5 n-3 | <LOD | <LOD | <LOD | <LOD |
| C22:5 n-3 | 0.32 | <LOD | <LOD | <LOD |
| Total Omega-3 | 99.27 | 97.97 | 98.94 | 98.86 |
| C18:3n-6 | <LOD | <LOD | 0.05 | <LOD |
| C20:3 n-6 | <LOD | <LOD | 0.13 | 0.11 |
| C20:4 n-6 | <LOD | 0.21 | 0.26 | 0.37 |
| Total Omega-6 | <LOD | 0.21 | 0.44 | 0.48 |

TABLE 1

| Parameter | Release Specification | Distilled oil [1] | Distilled oil [2] | PUFA product according to the invention [1] | PUFA product according to the invention [2] |
|---|---|---|---|---|---|
| Polyaromatic Hydrocarbons (PAH) (μg/kg) | | | | | |
| Benzo(a)pyrene Impurities | NMT 2.0 | 0.90 | 0.90 | <0.05 | <0.05 |
| Dioxins and Furans PCDDs and PCDFs[1] (pg WHO-PCDD/F-TEQ/g) | NMT 2.0 | 0.46 | 0.37 | 0.2 | 0.184 |
| PCBs (mg/kg) | NMT 0.09 | 0.0037 | 0.0103 | 0.0007 | 0.0012 |
| Sum of Dioxins, Furans and Dioxin-like PCBs[2] (pg WHO-PCDD/F-PCB-TEQ/g) | NMT 10.0 | 1.03 | 0.466 | 0.30 | 0.298 |

[1]Dioxin limits include the sum of polychlorinated dibenzeno-para-dioxins (PCDDs) and polychlorinated dibenzofurans (PCDFs) and expressed in World Health Organisation (WHO) toxic equivalents using WHO-toxic equivalent factors (TEFs). This means that analytical results relating to 17 individual dioxin congeners of toxicological concern are expressed in a single quantifiable unit: TCDD toxic equivalent concentration or TEQ
[2]Maximum for dioxin and Furans remains at 2 pg/g

Example 9

An EPA/DHA-rich product of the process of the present invention was compared with an EPA/DHA-rich oil produced by distillation. The wt % analysis of their component PUFAs is shown below.

| Fatty Acid | Maxomega Ethyl Ester (Omega-3 90 ethyl esters) Area % | Distilled Ethyl Ester (Omega-3 90 ethyl esters[1]) Area % |
|---|---|---|
| EPA (C20:5n-3) | 53.3 | 46.6 |
| DHA (C22:6n-3) | 32.9 | 38.2 |
| TOTAL EPA + DHA | 86.2 | 84.8 |
| C18:3 n-3 | 0.3 | 0.1 |
| C18:4 n-3 | 1.2 | 2.0 |
| C20:4 n-3 | 1.8 | 0.6 |
| C21:5 n-3 | 2.7 | 1.8 |
| C22:5 n-3 | 5.0 | 3.8 |
| Total Omega-3 | 97.2 | 93.1 |
| C18:2 n-6 | 0.2 | 0.1 |
| C18:3n-6 | <0.1 | 0.2 |
| C20:3 n-6 | <0.1 | 0.1 |
| C20:4 n-6 | 2.0 | 2.6 |
| C22:4 n-6 | <0.1 | 0.1 |
| C22:5 n-6 | 0.6 | 1.0 |
| Total Omega-6 | 2.8 | 4.1 |

The invention claimed is:

1. A chromatographic separation process for recovering a polyunsaturated fatty acid (PUFA) product, from a feed mixture, which process comprises introducing the feed mixture to a simulated or actual moving bed chromatography apparatus having a plurality of linked chromatography columns containing, as eluent, an aqueous alcohol, wherein the apparatus has a plurality of zones comprising at least a first zone and second zone, each zone having an extract stream and a raffinate stream from which liquid can be collected from said plurality of linked chromatography columns, and wherein (a) a raffinate stream containing the PUFA product together with more polar components is collected from a column in the first zone and introduced to a nonadjacent column in the second zone, and/or (b) an extract stream containing the PUFA product together with less polar components is collected from a column in the second zone and introduced to a nonadjacent column in the first zone, said PUFA product being separated from different components of the feed mixture in each zone.

2. A process according to claim 1, wherein part of one or more of the extract stream from the first zone, the raffinate stream from the first zone, the extract stream from the second zone, and the raffinate stream from the second zone are recycled back into the same zone, typically into an adjacent column in the same zone.

3. A chromatographic separation process according to claim 1 wherein (a) the aqueous alcohol eluent present in each zone has a different water:alcohol ratio; and/or (b) the rate at which liquid collected via the extract and raffinate streams in each zone is recycled back into the same zone is adjusted such that the PUFA product can be separated from different components of the feed mixture in each zone.

4. A chromatographic separation process according to claim 3, wherein the rate at which liquid collected via the extract stream out of the first zone is recycled back into the first zone differs from the rate at which liquid collected via the extract stream out of the second zone is recycled back into the second zone, and/or the rate at which liquid collected via the raffinate stream out of the first zone is recycled back into the first zone differs from the rate at which liquid collected via the raffinate stream out of the second zone is recycled back into the second zone.

5. A process according to claim 1, wherein the apparatus has a first zone and a second zone, said PUFA product being separated from less polar components of the feed mixture in the first zone, and said PUFA product being separated from more polar components of the feed mixture in the second zone.

6. A process according to claim 1, wherein the PUFA product comprises at least one ω-3 PUFA.

7. A process according to claim 6, wherein the PUFA product comprises EPA and/or DHA.

8. A process according to claim 1, wherein in addition to said PUFA product, an additional secondary PUFA product is recovered in the chromatographic separation process.

9. A process according to claim 8, wherein the PUFA product is EPA and the additional secondary PUFA product is DHA.

10. A process according to claim 1, wherein the chromatography columns contain, as adsorbent, substantially spherical beads.

11. A process according to claim 10, wherein the beads are formed from C18 bonded silica gel.

12. A process according to claim 10, wherein the substantially spherical beads have a diameter of from 250 to 500 µm.

13. A process according to claim 1, wherein the eluent is a mixture of water and a $C_1$-$C_6$ alcohol.

14. A process according to claim 13, wherein the $C_1$-$C_6$ alcohol is methanol or ethanol.

15. A process according to claim 1, wherein the eluent in the first zone contains more alcohol than the eluent in the second zone, and wherein the second zone is downstream of the first zone, with respect to the flow of eluent in the system.

16. A process according to claim 1, wherein the water:alcohol ratio of the eluent in the first zone is from 0.5:99.5 to 1.5:98.5 parts by volume, and the water:alcohol ratio of the eluent in the second zone is from 4.5:95:5 to 5.5:94.5 parts by volume.

17. A process according to claim 1, wherein the water:alcohol ratio of the eluent in the first and second zones is controlled by introducing water and/or alcohol into one or more columns in the first and second zones.

18. A process according to claim 2 wherein the rate at which liquid collected via the extract stream from the first zone is recycled back into the first zone is faster than the rate at which liquid collected via the extract stream from the second zone is recycled back into the second zone.

19. A process according to claim 5, comprising:
   (i) introducing the feed mixture into the first zone, and removing a first raffinate stream enriched with the PUFA product and a first extract stream depleted of the PUFA product, and
   (ii) introducing the first raffinate stream into the second zone, removing a second raffinate stream depleted of the PUFA product, and collecting a second extract stream to obtain the PUFA product.

20. A process according to claim 5, comprising:
   (i) introducing the feed mixture into the second zone, and removing a first raffinate stream depleted of the PUFA product and a first extract stream enriched in the PUFA product, and (ii) introducing the first extract stream into the first zone, removing a second extract stream depleted of the PUFA product and collecting a second raffinate stream to obtain the PUFA product.

21. A process according to claim 1, wherein the simulated or actual moving bed chromatography apparatus has fifteen chromatographic columns 1 to 15.

22. A process according to claim 5 wherein the first zone consists of eight adjacent columns 1 to 8.

23. A process according to claim 5, wherein the second zone consists of seven adjacent columns, 9 to 15.

24. A process according to claim 21, wherein (a) alcohol is introduced into column 1, and/or (b) alcohol is introduced into column 9, and/or (c) water is introduced into column 4, and/or (d) water is introduced into column 12.

25. A process according to claim 21, wherein aqueous alcohol is introduced into column 1 and/or column 9.

26. A process according to claim 21, wherein a first raffinate stream is collected from column 7 and introduced into column 13.

27. A process according to claim 1, wherein the apparatus has a first zone, a second zone and a third zone and wherein (a) the eluent in the first zone contains more alcohol than the eluent in the second and third zones and the first zone is upstream of the second and third zones with respect to the flow of eluent in the system and (b) the eluent in the second zone contains more alcohol than the eluent in the third zone and the second zone is upstream of the third zone with respect to the flow of eluent in the system, said PUFA product being separated in the first zone from components of the feed mixture which are less polar than the PUFA product, said PUFA product being separated in the second zone from components of the feed mixture which are less polar than the PUFA product but more polar than the components separated in the first zone, and said PUFA product being separated in the third zone from components of the feed mixture which are more polar than the PUFA product.

* * * * *